(12) United States Patent
Hassidov et al.

(10) Patent No.: US 8,398,540 B2
(45) Date of Patent: Mar. 19, 2013

(54) SEMI DISPOSABLE ENDOSCOPE

(75) Inventors: Noam Hassidov, Bustan Hagalil (IL);
Daniel Glozman, Kefar Adummim (IL);
Moshe Shoham, Hoshaya (IL)

(73) Assignee: Technion Research & Development Foundation Ltd., Senate House, Technion, Haifa (IL)

( * ) Notice: Subject to any disclaimer, the term of this patent is extended or adjusted under 35 U.S.C. 154(b) by 578 days.

(21) Appl. No.: 12/599,469

(22) PCT Filed: May 11, 2008

(86) PCT No.: PCT/IL2008/000644
§ 371 (c)(1),
(2), (4) Date: Apr. 26, 2010

(87) PCT Pub. No.: WO2008/139461
PCT Pub. Date: Nov. 20, 2008

(65) Prior Publication Data
US 2010/0204546 A1    Aug. 12, 2010

Related U.S. Application Data

(60) Provisional application No. 60/924,350, filed on May 10, 2007, provisional application No. 61/013,590, filed on Dec. 13, 2007.

(51) Int. Cl.
*A61B 1/00* (2006.01)
(52) U.S. Cl. .......... 600/109; 600/129; 600/175
(58) Field of Classification Search .......... 600/101, 600/109–112, 129, 175
See application file for complete search history.

(56) References Cited

U.S. PATENT DOCUMENTS

| | | | |
|---|---|---|---|
| 3,610,240 | A | 10/1971 | Harautuneian |
| 4,219,013 | A | 8/1980 | Okada |
| 4,646,722 | A | 3/1987 | Silverstein et al. |
| 4,741,326 | A | 5/1988 | Sidall et al. |
| 5,144,848 | A | 9/1992 | Uenishi et al. |
| 5,554,097 | A | 9/1996 | Guy |
| 5,704,892 | A | 1/1998 | Adair |

(Continued)

FOREIGN PATENT DOCUMENTS

| | | |
|---|---|---|
| CN | 1277506 | 10/2006 |
| EP | 1765146 B1 | 4/2009 |

(Continued)

OTHER PUBLICATIONS

PCT International Search Report and Written Opinion of the ISA, mailed Jan. 7, 2009 in PCT/IL2008/000644.

(Continued)

*Primary Examiner* — W. B. Perkey
(74) *Attorney, Agent, or Firm* — Daniel J. Swirsky; AlphaPatent Associates Ltd.

(57) ABSTRACT

A disposable endoscope body having an enclosure in its distal end for a non-disposable element, such as a video camera head. Because of its complexity and sensitivity, the camera head is non-disposable and cannot be sterilized. The camera head is sealed in the endoscope body, such that it does not contaminate the patient during the procedure. Sealing is achieved using an end cap. After use, the camera is withdrawn from the proximal end of the endoscope, which, being near to or within the workstation, has not been inserted into the subject and should be free of patient contamination. Passage of the camera out through the proximal end therefore avoids contamination by the patient, such that it can be used again without need for sterilization. A dispensing kit is described, for supplying the sterile endoscope body and for installing and sealing the camera with a minimum of manual intervention.

15 Claims, 22 Drawing Sheets

U.S. PATENT DOCUMENTS

| | | | |
|---|---|---|---|
| 5,868,664 A | 2/1999 | Speier et al. | |
| 5,876,329 A | 3/1999 | Harhen | |
| 5,906,591 A | 5/1999 | Dario et al. | |
| 6,485,409 B1 | 11/2002 | Voloshin et al. | |
| 6,517,477 B1 | 2/2003 | Wendlandt | |
| 6,621,005 B1 | 9/2003 | Lovec et al. | |
| 6,939,291 B2 | 9/2005 | Phee Soo Jay et al. | |
| 7,691,056 B2 * | 4/2010 | Hirata | 600/129 |
| 7,713,189 B2 * | 5/2010 | Hanke | 600/109 |
| 2003/0065250 A1 | 4/2003 | Chiel et al. | |
| 2003/0097043 A1 | 5/2003 | Ouchi et al. | |
| 2005/0014996 A1* | 1/2005 | Konomura et al. | 600/175 |
| 2007/0009376 A1 | 1/2007 | Hamada et al. | |
| 2007/0066869 A1 | 3/2007 | Hoffman | |
| 2007/0255101 A1 | 11/2007 | Bar-Or | |
| 2010/0204546 A1* | 8/2010 | Hassidov et al. | 600/114 |

FOREIGN PATENT DOCUMENTS

| | | |
|---|---|---|
| JP | 03-231623 A | 10/1991 |
| JP | 04-236964 A | 8/1992 |
| JP | 07-116112 A | 5/1995 |
| JP | 2006-141935 A | 6/2006 |
| WO | 2004/016299 | 2/2004 |
| WO | 2005/110185 | 11/2005 |
| WO | WO 2005/115221 A1 * | 12/2005 |
| WO | 2006/025058 | 3/2006 |
| WO | 2007/017876 | 2/2007 |
| WO | 2007/029230 | 3/2007 |
| WO | 2007/093994 | 8/2007 |
| WO | 2008/096365 | 8/2008 |
| WO | 2008/099389 | 8/2008 |

OTHER PUBLICATIONS

Extended European Search Report, issued on Aug. 2, 2102, in corresponding European Application No. 08751342.0.

* cited by examiner

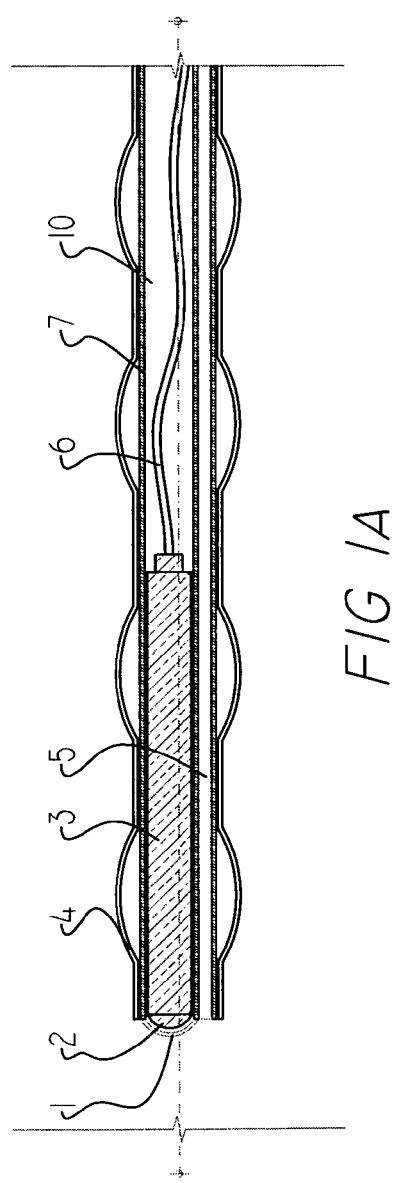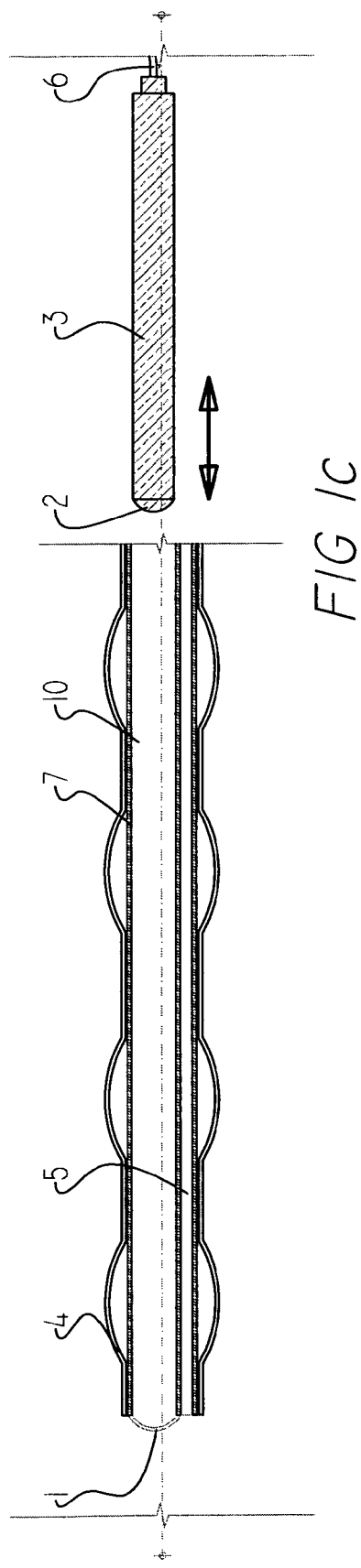

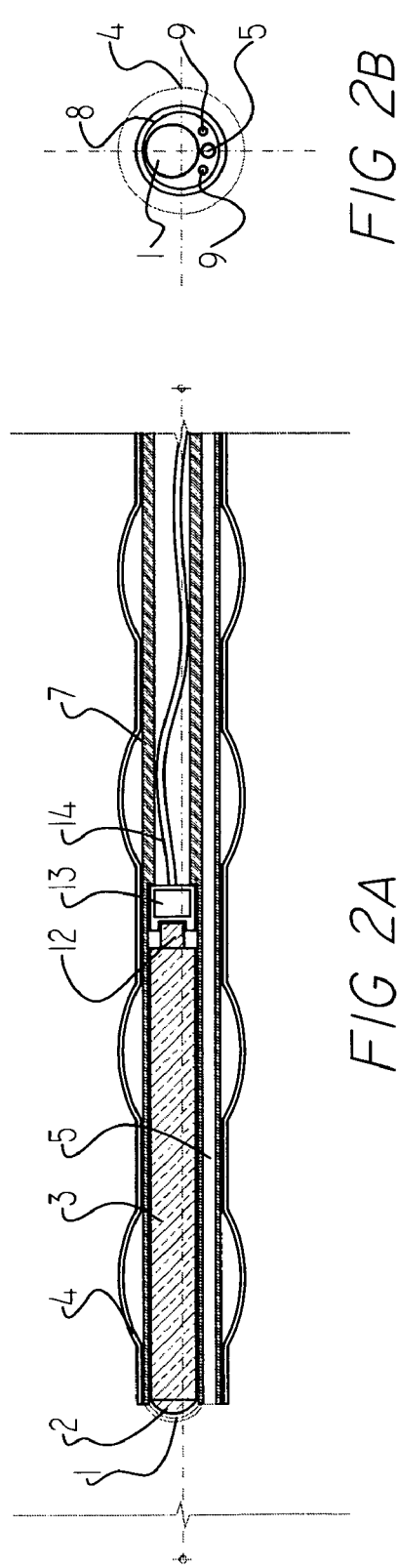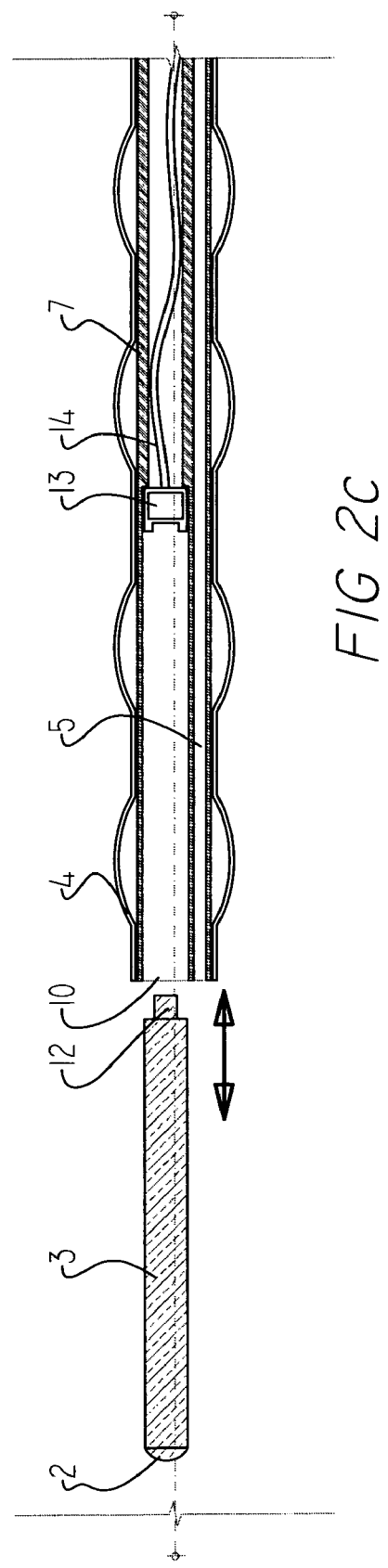

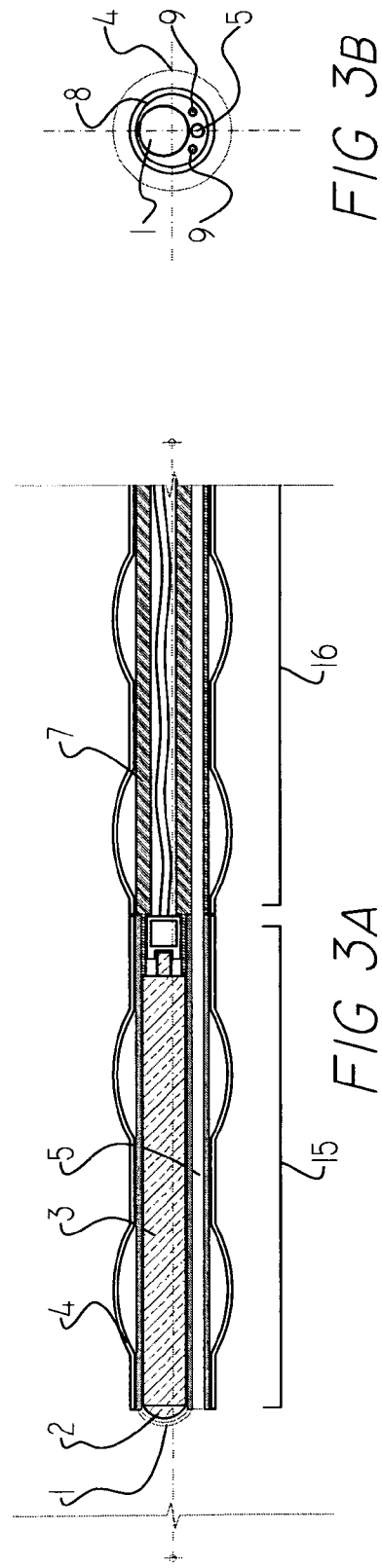
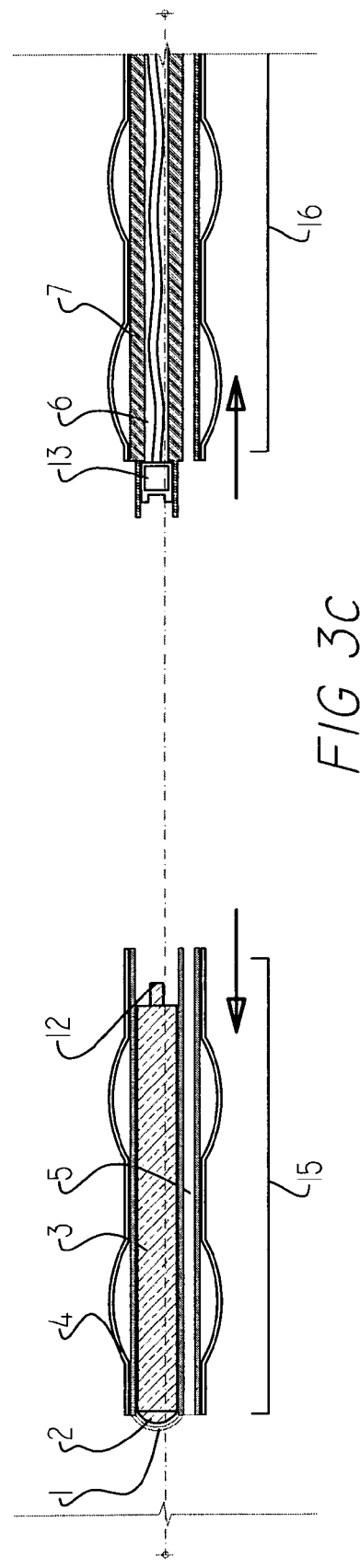
FIG 3A
FIG 3B
FIG 3C

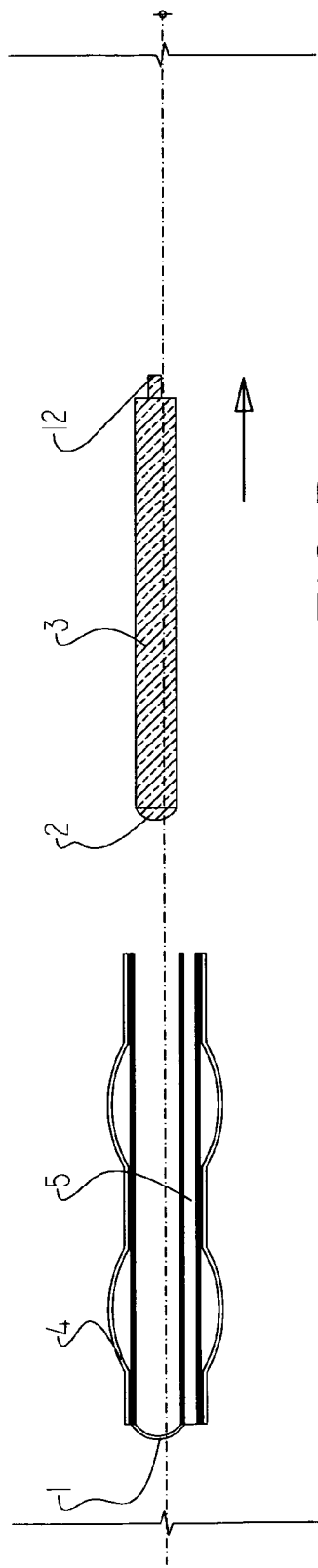
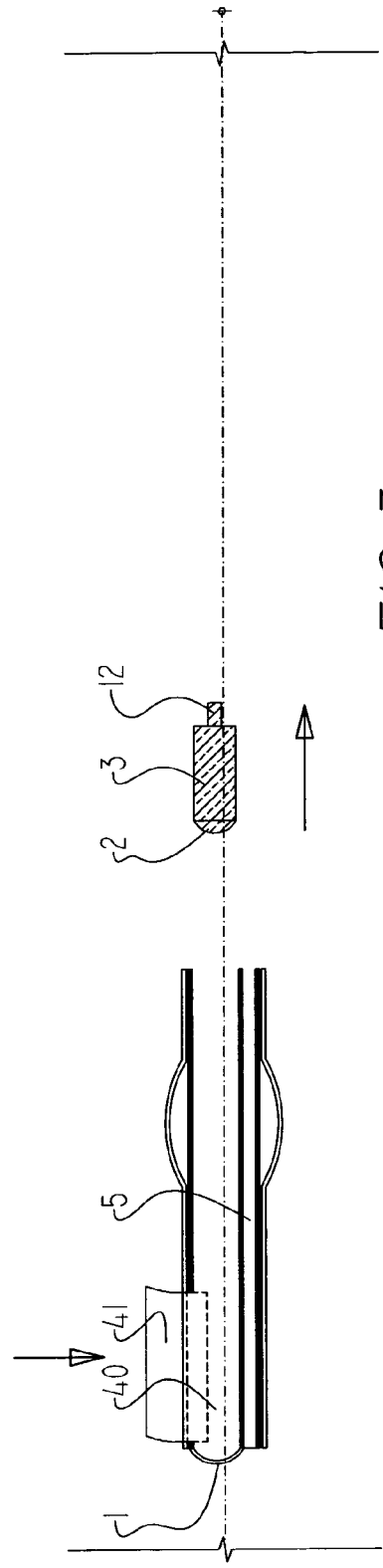

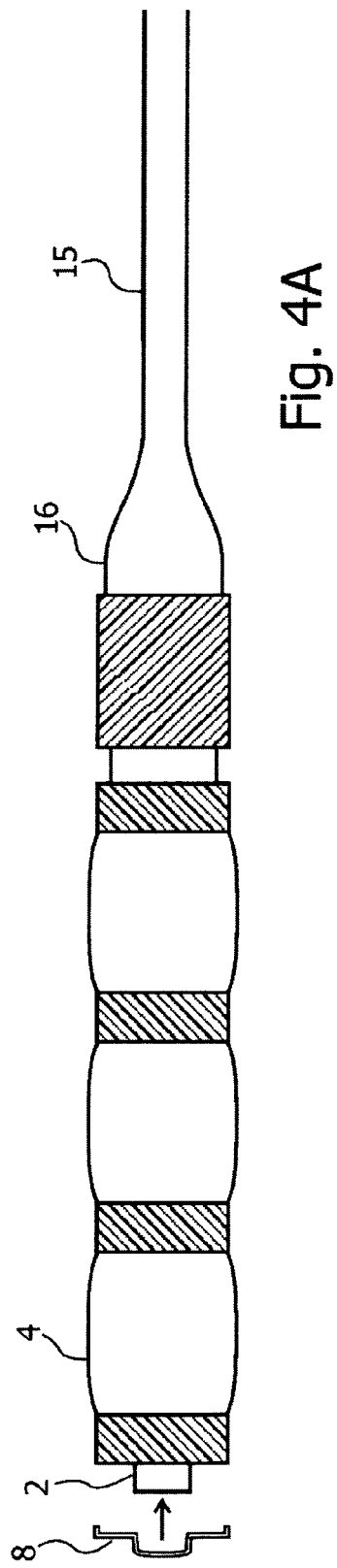
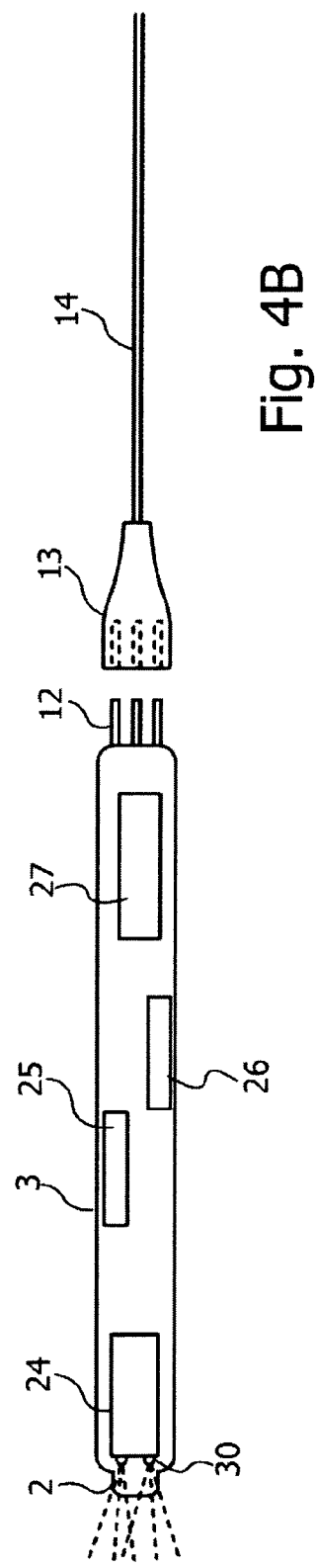
Fig. 4A
Fig. 4B

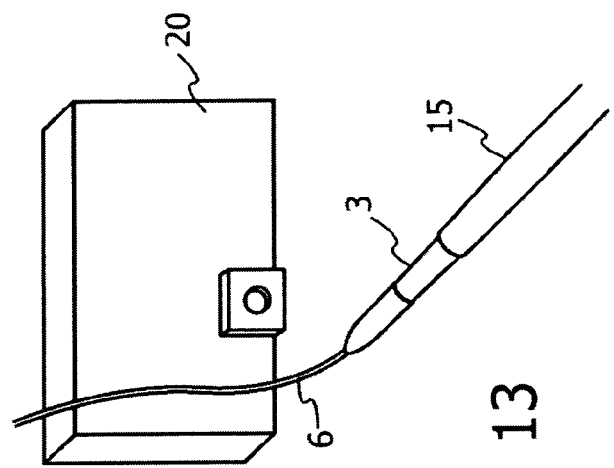
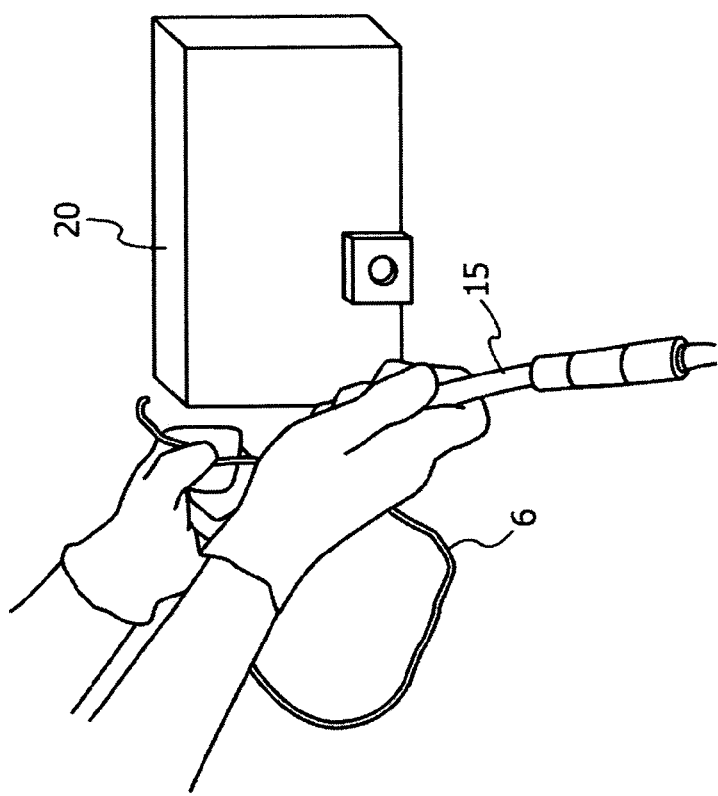

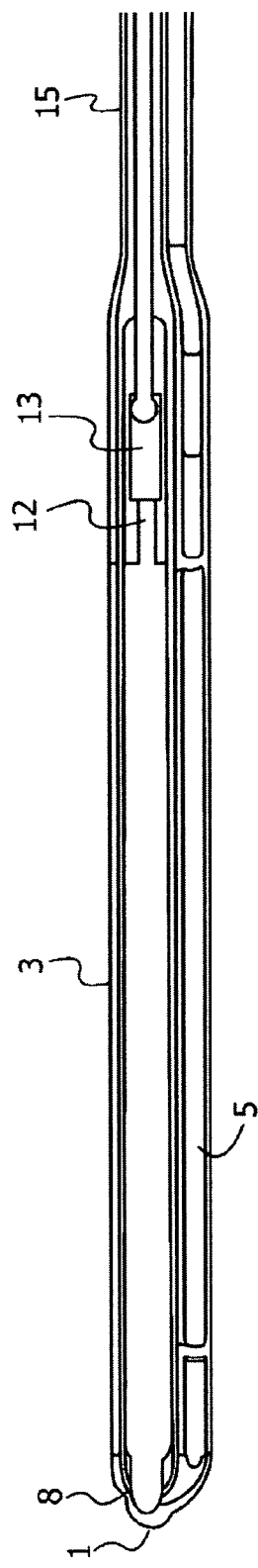
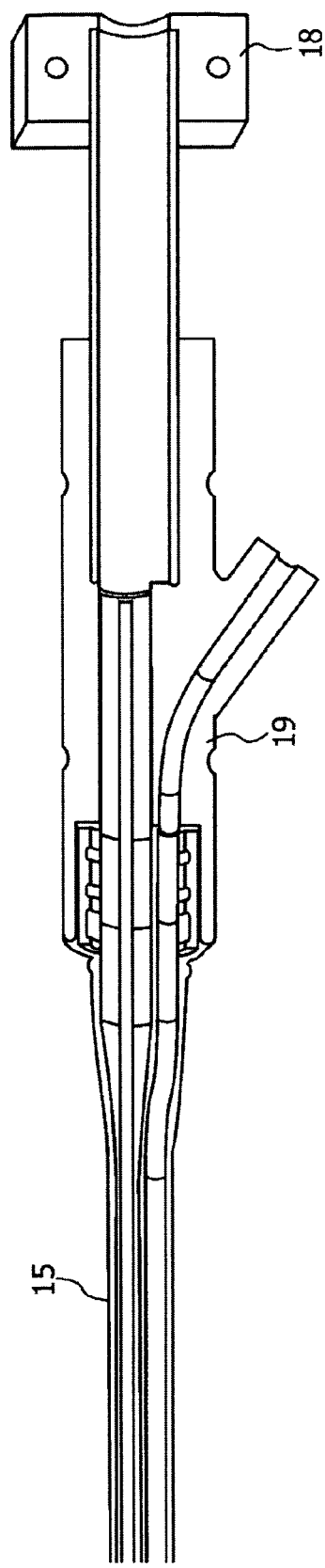
Fig. 14
Fig. 15

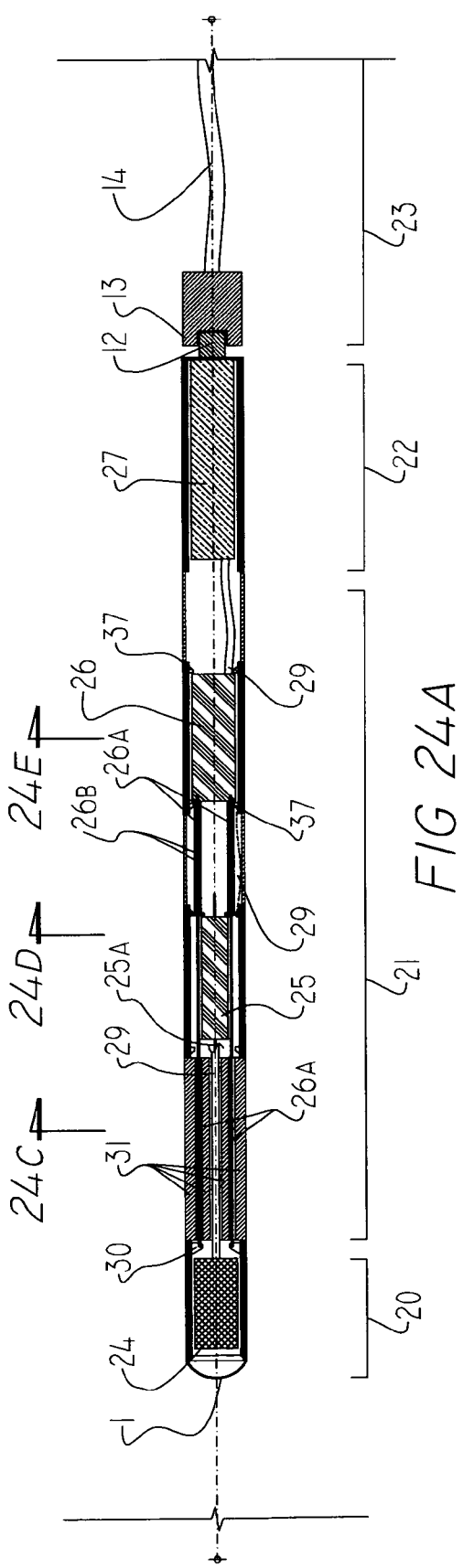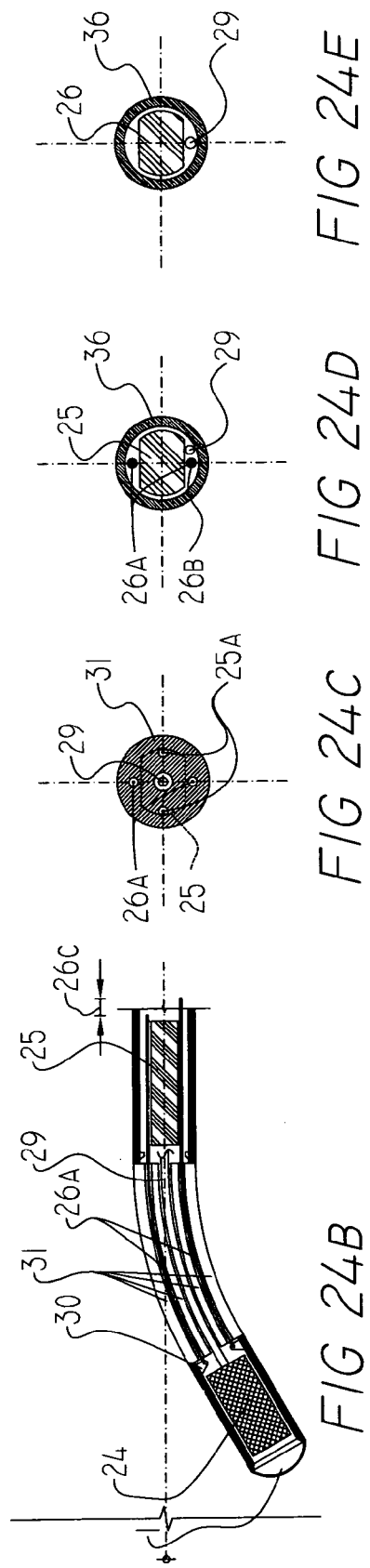
FIG 24A
FIG 24B
FIG 24C
FIG 24D
FIG 24E

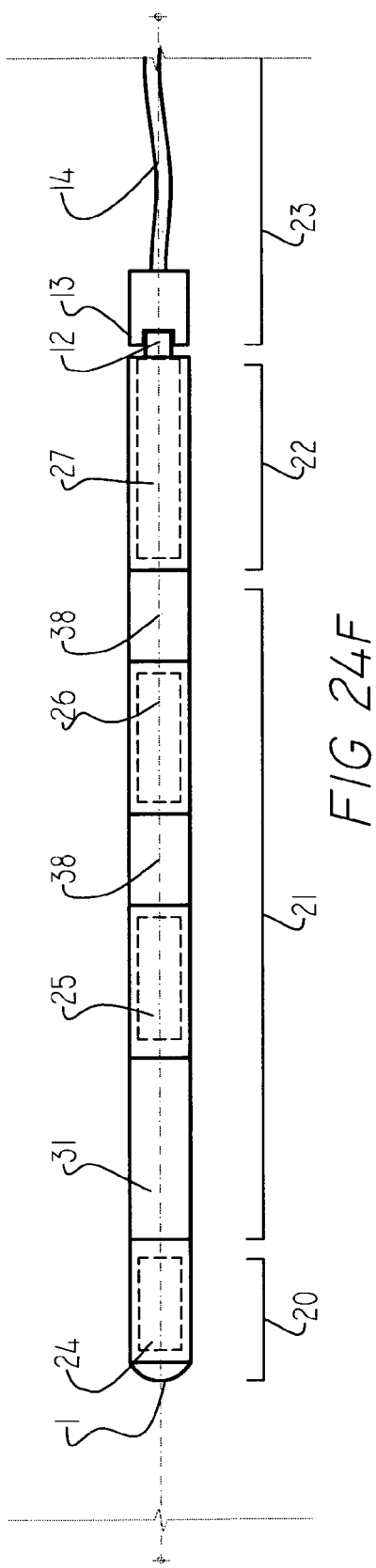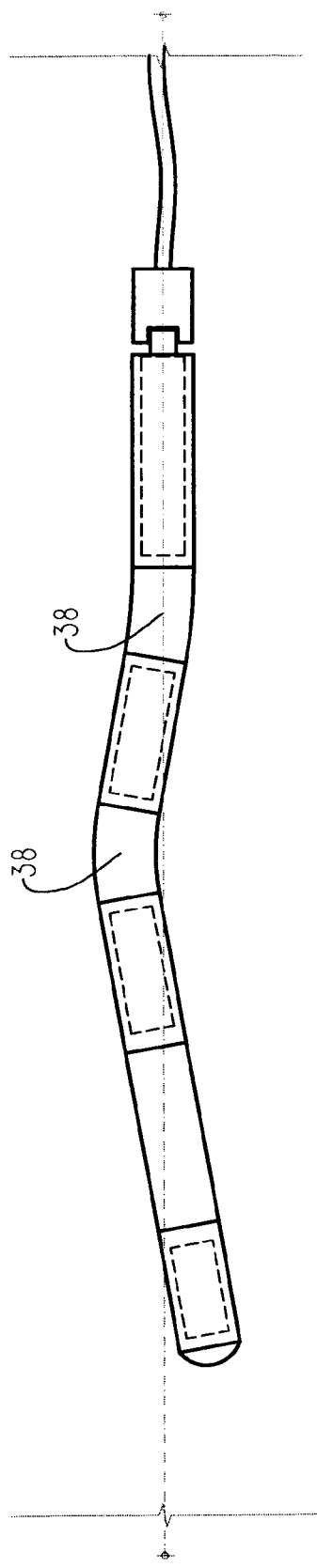

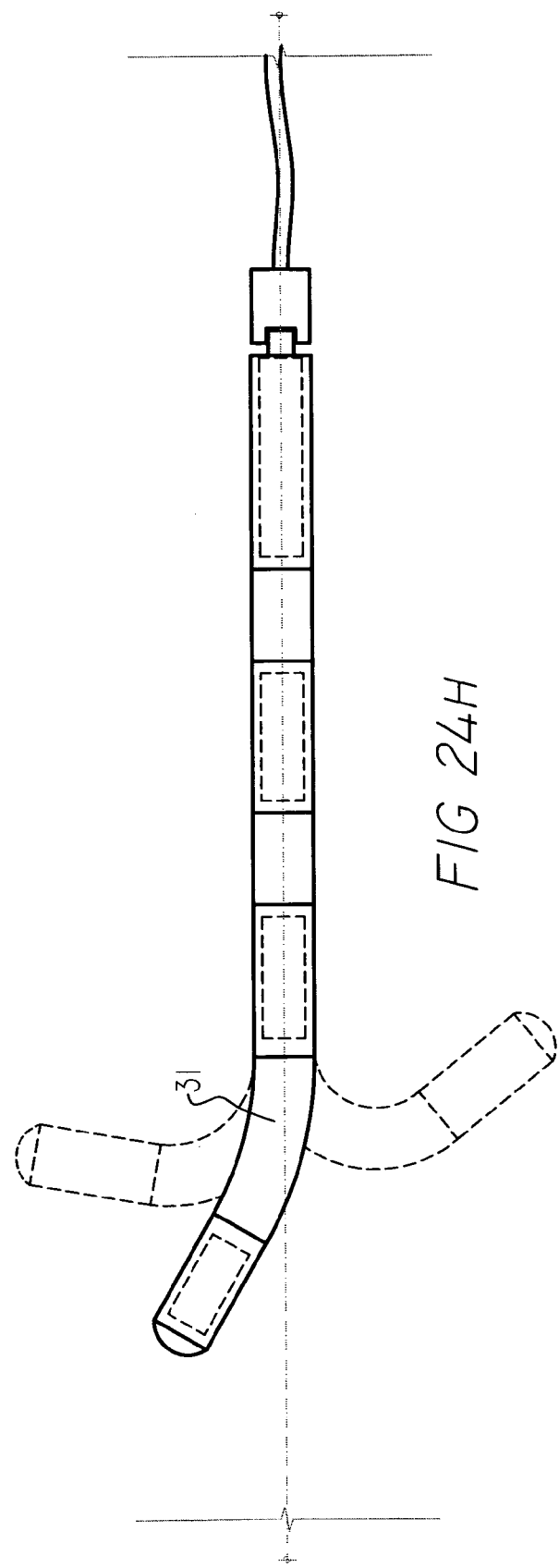

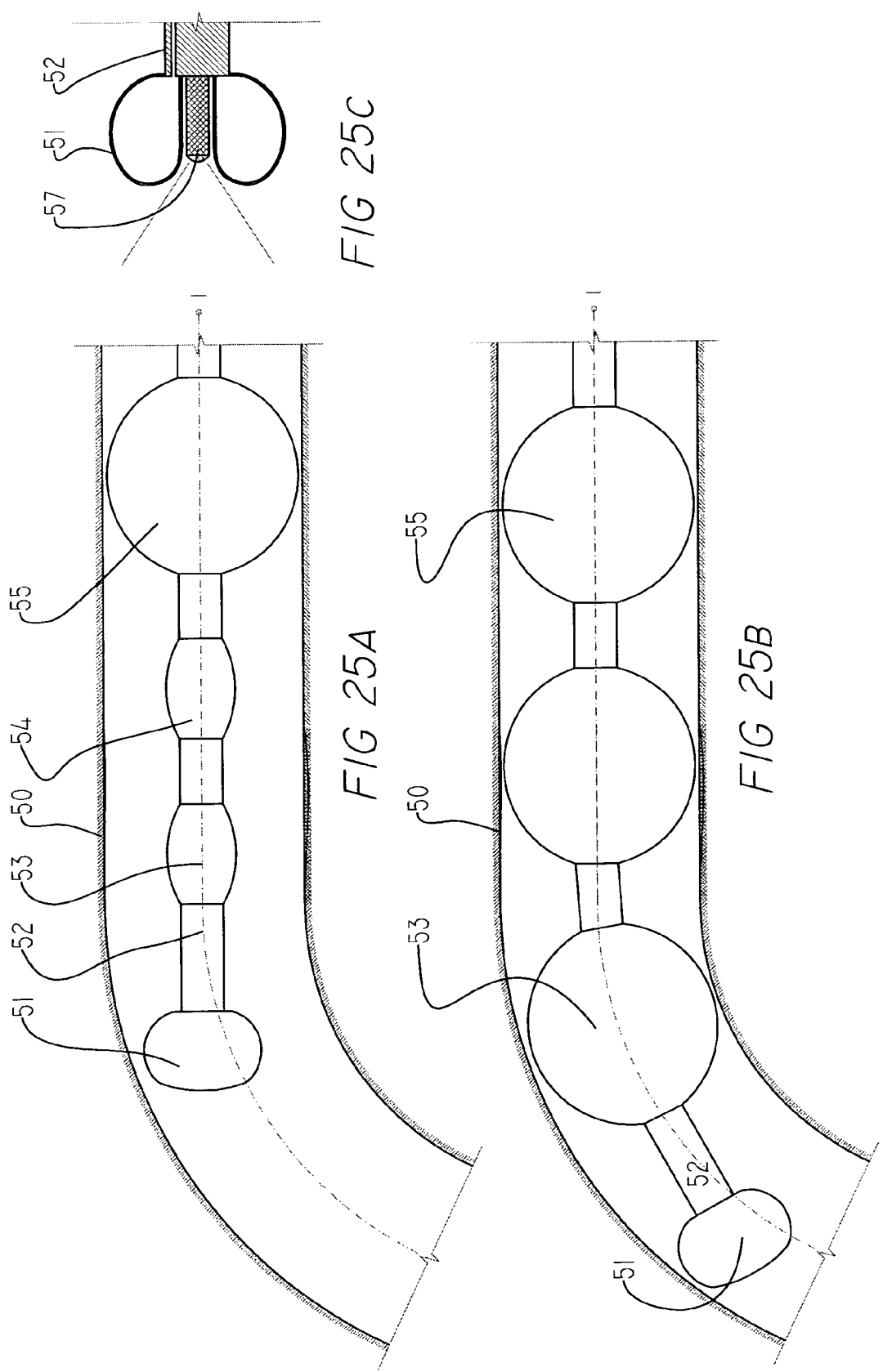

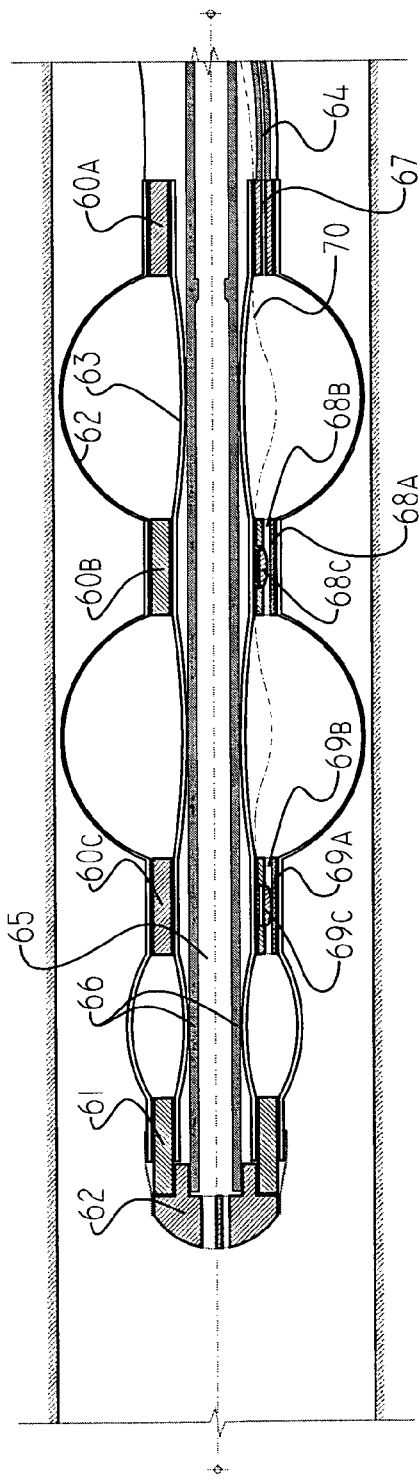
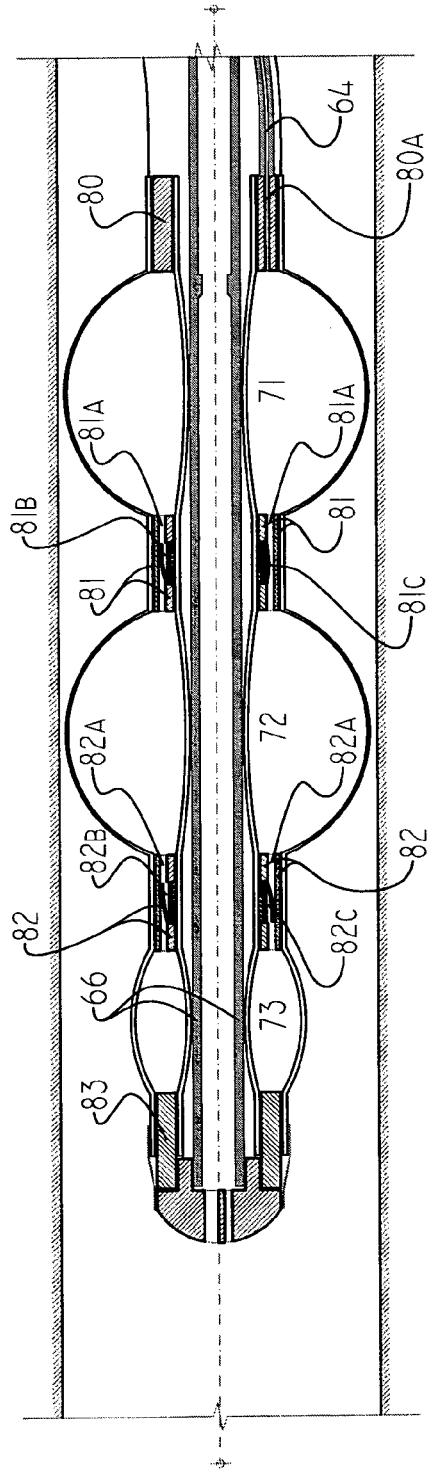

SEMI DISPOSABLE ENDOSCOPE

This application is a U.S. National Phase Application under 35 U.S.C. 371 of PCT International Application No. PCT/IL2008/000644, which has an international filing date of May 11, 2008, and which claims benefit from U.S. Provisional Patent Application No. 60/924,350, filed May 10, 2007, and U.S. Provisional Patent Application No. 61/013,590, filed Dec. 13, 2007, the contents of which are hereby incorporated in their entirety by reference.

FIELD OF THE INVENTION

The present invention relates to the field of endoscopes, especially those made up of low cost disposable elements incorporating high cost, multi-use, non-disposable elements, and methods of using both while maintaining sterility and preventing cross-contamination of patients.

BACKGROUND OF THE INVENTION

Flexible endoscopes in general and colonoscopes in particular are difficult to clean and disinfect thoroughly, leading to potential problems of cross-contamination between patients and between patients and staff. Additionally, such endoscopes often use expensive devices such as camera heads, electro-mechanical steering devices, and control electronics modules, which cannot be readily sterilized, and because of their cost, cannot be discarded after every use. These problems can be partially avoided by covering the endoscope with a single-use sleeve, into which the unsterilized endoscope may be inserted, and which can be disposed of after use, leaving the endoscope ready for the next procedure after insertion into a fresh sterile sleeve. This use of a disposable sleeve (also referred to as a sheath) to cover an endoscope is well known in the art.

There exist many prior art devices which address these problems. Some such prior art devices are described in patents or patent applications WO2007/093994, US2007/0255101, WO2007/029230, WO2006/025058, WO2005/110185, WO2004/016299, U.S. Pat. No. 6,485,409, U.S. Pat. No. 4,741,326, U.S. Pat. No. 4,646,722, U.S. Pat. No. 5,876,329, CN1,486,666 and US2003/0097043.

The disclosures of each of the publications mentioned in this section and in other sections of the specification, are hereby incorporated by reference, each in its entirety.

SUMMARY OF THE INVENTION

The present disclosure describes a number of examples of endoscopic apparatus divided into parts that have to come into direct contact with the body and parts that do not have to come into direct contact with the body. Elements that do not have to come into direct contact with the body are often costly parts, such as the camera and/or steering components, or other internal modules for implementing some of the functionalities of the endoscopic apparatus. Elements that have to come into direct contact with the body may include the endoscopic outer housing with or without propulsion elements, a working channel, a suction channel, water and/or air supply channels for camera washing and colon inflation, electrical control or data wiring and connectors. The parts which come into contact with the body are generally made to be disposable, such that the cost of sterilization is obviated, and the danger of improper sterilization reduced. The parts that do not come into contact with the body are generally non-disposable. Such endoscopes are termed in this application, semi disposable endoscopes, to illustrate the partly disposable and partly non-disposable nature of the endoscopes described herein.

One example of such endoscopes comprises a disposable endoscope body, having an enclosure in its distal end for incorporating a non-disposable element which can incorporate one or more functional units, such as a video camera head, an electronic or magnetic or ultrasound probe, an electro-mechanical steering head, a spectral imaging device, a digital signal processing unit, or any such similar functional component, generally having comparatively high cost and complexity. Because of its complexity, cost and sensitivity, the non-disposable part cannot generally be sterilized. According to one exemplary implementation described in this application, the non-disposal element may be inserted into the endoscope from the distal end, and sealed in its disposable or sterilizable enclosure during use, such that it does not contaminate the patient during the procedure. The sealing may be achieved using an end sealing cap. After use, the non-disposal element may be withdrawn from the proximal end of the endoscope, which, being near to or within the workstation, has not been inserted into the subject and should not therefore be considered as being contaminated by the subject. Passage of the non-disposal element out through this non-contaminated end of the endoscope therefore avoids its contamination by the subject, such that it can be used again, advisedly with surface cleaning or disinfection, but without the need for sterilization. According to other exemplary implementations, the non-disposable element may be inserted and withdrawn from the proximal end of the endoscope.

According to another aspect of the present invention, packaging apparatus and methods are described, by which a sterile disposable endoscope is delivered in a sealed sterile package, together with a sterile end-cap mounted in a novel dispensing unit, such that the sterile outer surface of the disposable endoscope is protected from contact with the unsterilized non-disposal element during insertion of the non-disposal element into the endoscope. Furthermore, the packaging apparatus and methods include a dispenser and its use that enables the sealing end cap to be applied under sterile conditions. The disposable endoscope itself is discarded after use.

Some advantages of the semi-disposable endoscopes described in this disclosure are that:
1. Only sterile parts contact the patient's body.
2. There is no risk of cross-contamination.
3. Simple assembly and disassembly are possible.
4. Simplicity and low cost of the disposable parts, optionally including locomotion mechanism.
5. Costly, non-disposable elements that cannot readily be sterilized can be repeatedly used, without fear of contamination or cross-contamination.

The disposable part of the endoscopic device can include it own propulsion unit, and particularly convenient examples of such a unit are the self-propelled, inflatable devices such as are shown in the various embodiments described in published PCT Application WO 2007/017876 for "Tip Propelled Device for Motion through a Passage", in PCT Application No. PCT/IL2008/000180 for "Inflatable Balloon Device for Motion through a Passage" and in PCT Application No. PCT/IL2008/000173 for "Inflatable Balloon Device and Applications", all to the present applicants. However, it is to be understood that the presently claimed invention is not intended to be limited to endoscopes having such propulsion units, which are shown only as convenient examples, but is intended to include semi-disposable endoscopes having other types of propulsion mechanisms, or no propulsion mechanism at all.

There is thus provided in accordance with a first example described in this disclosure, a an endoscope comprising:
(i) an elongate housing having a compartment at its distal end, the compartment having an entrance aperture and a first connector part disposed at its proximal end,
(ii) a flexible connecting link attached to the first connector part and running proximally down the elongate housing to its proximal extremity,
(iii) an endoscopic element adapted to be inserted into the compartment through the entrance aperture, the element having a second connector part which mates with the first connector part when the endoscopic element is inserted into the compartment, and
(iv) a seal element for sealing the compartment, such that after the endoscopic element is inserted into the compartment, application of the seal element provides isolation between the endoscopic element and the environment outside the distal end of the endoscope.

In such an endoscope, the flexible connecting link may be either an electric cable or a mechanical cord. Furthermore, the connector parts may be such that insertion of the endoscopic element into the compartment enables the endoscopic part to be withdrawn by pulling on the flexible connecting link.

In such examples of endoscopes, the compartment aperture may be located in the axial end of the elongate housing, and the endoscope element inserted axially, in which case the seal element should be an end cap. Alternatively, the compartment aperture may be located in a wall at a distal part of the elongate housing, and the endoscope element inserted laterally, in which case the seal element should be a surface seal.

In any of the above-described endoscopes, the endoscope element may be adapted for multiple use, while the elongate housing may be adapted for a single-use. In the latter case, it would be advantageous if the elongate housing were adapted to be affected during insertion or withdrawal of the endoscope element, such that it cannot be used again.

In any of the above-described examples of endoscopes, the compartment, when sealed, should isolate the endoscope element from the environment outside of the endoscope. According to this arrangement, the endoscopic element can be used in a non-sterile condition in the endoscope without generating contamination outside the endoscope. Furthermore, the elongate housing may be constructed such that the endoscopic element can be withdrawn from the elongate housing without making contact with that part of the outer surface of the elongate housing which has been inserted into a subject.

According to further examples of the endoscopes described in this disclosure, the endoscopic element may comprise a camera head or a steering mechanism. Additionally, the endoscope may further comprise at least one channel running through the elongate housing, the at least one channel being isolated from the compartment. In such a case, the at least one channel may be any one of a working channel, an irrigating channel and a gas supply channel.

Other implementations of such endoscopes may further include a propulsion unit for propelling the endoscope. Such a propulsion unit may comprise a series of connected sequentially inflated balloons.

Yet other implementations described in this application may involve an endoscope comprising:
(i) an elongate housing having a compartment at its distal end, the compartment having an entrance aperture,
(ii) an endoscopic element adapted to be inserted into the compartment through the entrance aperture, the element having a flexible connecting link attached to its proximal end, the flexible link being of length such that it extends to the proximal end of the elongate housing when the endoscopic element is inserted into the compartment, and
(iii) a seal element for sealing the compartment, such that after the endoscopic element is inserted into the compartment, application of the seal element provides isolation between the endoscopic element and the environment outside the distal end of the endoscope.

In such an implementation, the flexible connecting link may be any one of an electric cable, a cord, and a fluid conveying tube, and is adapted to enable the endoscopic element to be withdrawn proximally from the elongate housing by pulling on the flexible connecting link.

In such examples of endoscopes, the compartment aperture may be located in the axial end of the elongate housing, and the endoscope element inserted axially, in which case the seal element should be an end cap. Alternatively, the compartment aperture may be located in a wall at a distal part of the elongate housing, and the endoscope element inserted laterally, in which case the seal element should be a surface seal.

According to yet a further aspect of the present invention, a method of using an endoscope is described, comprising:
(i) providing an elongate housing having at its distal end, a compartment with a sealable entrance aperture,
(ii) inserting into the compartment an endoscope element,
(iii) sealing the entrance aperture,
(iv) performing an endoscopic procedure on a subject, and
(v) withdrawing the endoscopic element from the proximal end of the elongate housing, such that the endoscopic element does not contact those parts of the endoscope that were in contact with tissues of the subject during the procedure.

Such a method may also include the step of cleaning the endoscope element externally before insertion into another elongate housing. Furthermore, the step of inserting the endoscope element into another elongate housing of an endoscope may be performed without sterilizing the endoscope element.

In the endoscopes used in such methods, the endoscope element may have a flexible connecting link attached thereto, the flexible link being threaded down the elongate housing, such that withdrawing the endoscopic element from the proximal end of the elongate housing is performed by use of the flexible connecting link. In such a case, the flexible connecting link may be any one of an electric cable, a cord, and a fluid conveying tube. The flexible connecting link may be attached to the endoscope element through a mating connector pair, in which case one part of the mating connector pair should be disposed on the endoscope element, and the other part in the elongate housing, such that the connector parts are mated by insertion of the endoscope element into the compartment.

In yet another aspect of the invention described in this disclosure, there is described a kit for dispensing a sterile endoscope, the kit comprising a sterile tray covered by a protective layer, and the tray comprising:
(i) a sterile endoscope housing having at its distal end, a compartment with a sealable entrance aperture, and
(ii) a sterile sealing cap mounted on a hinged carrier in a dispensing unit disposed in proximity to the entrance aperture,
wherein the endoscope housing and the dispensing unit may be disposed such that the sterile sealing cap can be applied to the entrance aperture by rotation of the hinged carrier.

In such a kit, the sealable entrance aperture of the compartment may advantageously be uncovered to enable insertion of the endoscope element into the compartment after removal of that portion of the protective layer over the dispensing unit. Accordingly, the entrance aperture may be the only part of the endoscope housing to be exposed after removal of the portion of the protective layer over the dispensing unit, and may also be the only part of the endoscope housing to be exposed during insertion of the endoscope element.

These above-described kits may be adapted to enable insertion and sealing of the endoscope element into the endoscope housing without the endoscope element having any contact with the outer surface of the endoscope housing. Consequently, the endoscope element may have contact only with the entrance aperture of the endoscope housing.

Additionally, after application, the sterile sealing cap should be such as to isolate the endoscope element and the entrance aperture from the outside environment. With any of these kits, after removal of that portion of the protective layer from over the dispensing unit, the remainder of the protective layer, until removed for use of the endoscope, should provide isolation of the endoscope with the endoscope element sealed inside.

Additional implementations can include a steerable endoscope comprising:
(i) a flexible section disposed proximate the distal end of the endoscope,
(ii) at least one motion actuator disposed proximally to the flexible section, and
(iii) at least one wire attached between the motion actuator and the distal end of the endoscope element, the motion actuator being adapted to apply at least one of pushing and pulling action to the at least one wire, such that the flexible section bends in accordance with the action of the at least one wire.

In such a steerable endoscope, the at least one motion actuator may be at least two motion actuators, such that the flexible section can bend in a plurality of planes. The at least one motion actuator may further be an electric motor, and in any case, it may be controlled through either one of an electric cable or wirelessly. Such a steerable endoscope may further comprise a rotator to provide rotational motion to at least some of the wires, such that the distal end of the endoscope can be rotated.

Yet another exemplary endoscope may comprise an inflatable balloon disposed at its distal end, the diameter of the inflatable balloon being adjusted by inflation such that the inflatable balloon steers the tip of the endoscope into a bend of a lumen being traversed by the endoscope. In these exemplary endoscopes the inflatable balloon may be inflated or deflated on demand, in accordance with the bend in the lumen being traversed. Alternatively, the inflatable balloon can be inflated or deflated automatically according to input information about the curvature of the lumen, such that the endoscope has self steering properties.

According to yet further implementations of the presently described invention, there is provided a self-propelled device for locomotion through a lumen, comprising:
(i) a set of serially arranged inflatable chambers, each pair of adjacent chambers being connected by at least a first and a second connecting passage providing fluid communication between each of the pairs, and
(ii) a fluid source attached to a proximal end of the set of serially arranged inflatable chambers, such that the set of chambers inflate sequentially,
wherein each of the first and second connecting passages between a pair of adjacent chambers comprises a one-way flow valve, the valves in the first and second passages being oriented such that they open in response to oppositely directed fluid flow, and wherein the valves are maintained in an open position only when the pressure difference across them exceeds a predetermined value. The predetermined pressure difference may be that generated by the excess pressure in a fully inflated balloon over that of an uninflated balloon. In such a self-propelled device for locomotion through a lumen, the valves may remain open until flow commences in a direction opposite to that which holds the valves open. At least two of the valves may be actuated by pressure differences existing between their input and output sides.

An alternatively described self-propelled device for locomotion through a lumen, comprises:
(i) a set of serially arranged inflatable chambers, each pair of adjacent chambers being connected by at least one connecting passage providing fluid communication between each of the pairs, and
(ii) a fluid source attached to a proximal end of the set of serially arranged inflatable chambers, such that the set of chambers inflate sequentially,
wherein at least one of the connecting passages between each pair of adjacent chambers may comprise an electrically actuated valve, such that inflation and deflation of the chambers is controlled by electrical signals applied to the valves.

In such a self-propelled device, the at least one valve may be electrically actuated by a remotely applied signal.

According to yet another aspect of the invention described in this disclosure, there is provided a self-propelled endoscope housing for locomotion through a lumen, comprising:
(i) a set of serially arranged inflatable chambers, each pair of adjacent chambers being connected by at least one connecting passage providing fluid communication between each of the pairs,
(ii) a fluid source attached to a proximal end of the set of serially arranged inflatable chambers, such that the set of chambers inflate sequentially,
(iii) an axial compartment at the distal end of the endoscope housing, the compartment being sealed to the distal end of the endoscope housing and accessible from the proximal end of the endoscope housing, and
(iv) an endoscopic element having a flexible connecting link attached to its proximal end, and adapted to be inserted from the proximal end of the endoscope,
wherein the flexible connecting link enables the endoscope element to be withdrawn from the endoscope housing only through its proximal end. In such an endoscope, the flexible connecting link may be either an electric cable or a mechanical cord.

It is to be understood that throughout this application, the terms distal and proximal, as stated in the disclosure and as claimed, are intended to refer to that end of the element being described relative to the insertion of the element into a passage of a subject. In other words, the term distal refers to the forward end of the element in the direction in which it is intended to be inserted, and proximal refers to the rear end of the element, namely that towards the working station extremity. This is intended to refer both to the complete endoscope, and to any insert or part thereof.

BRIEF DESCRIPTION OF THE DRAWINGS

The present claimed invention will be understood and appreciated more fully from the following detailed description, taken in conjunction with the drawings in which:

FIGS. 1A-1C show schematically the overall construction of one example of a semi-disposable endoscope of the present application;

FIGS. 2A-2C show schematically another method of construction and assembly of such a semi-disposable endoscope, in which the non-disposable payload is inserted from the distal end of the endoscope device;

FIGS. 3A-3D show a schematically semi-disposable endoscope, in which the non-disposable element is inserted between the head and tail of the device;

FIG. 3E illustrates schematically a further example of a semi-disposable endoscope in which the non-disposable element is inserted distally into its enclosure through an aperture in the side wall of the endoscope housing, but is withdrawn proximally;

FIG. 4A shows a schematic disposable endoscope housing with a propulsion head using locomotion balloons; FIG. 4B shows an exemplary camera head for mounting therein;

FIGS. 10 to 13 show schematically novel methods of dismounting a semi-disposable endoscope of the type described in the above Figures, and removal of the non-disposable camera head from it such that there is no contamination of the non-disposable camera head by contact with the outer surface of the used endoscope;

FIGS. 14 and 15 illustrate schematic cut-away views of a semi-disposable endoscope such as those described in the previous figures, to illustrate the internal structure thereof;

FIGS. 24A-24H are schematic views of a non-disposable element of the type shown in FIG. 4B, incorporating a set of electrical motors for steering the front tip of the endoscope;

FIGS. 25A-25C illustrate schematically another exemplary aspect of the present invention, for providing self-adjusting and self-navigating properties to an endoscope; and FIGS. 26A-26B illustrate schematically more examples of inflatable chamber locomotion mechanisms for endoscopes, using orifice flow control, whether direct or by means of one-way valves, to control the inflation and deflation of the balloons.

DETAILED DESCRIPTION

Figure 6:
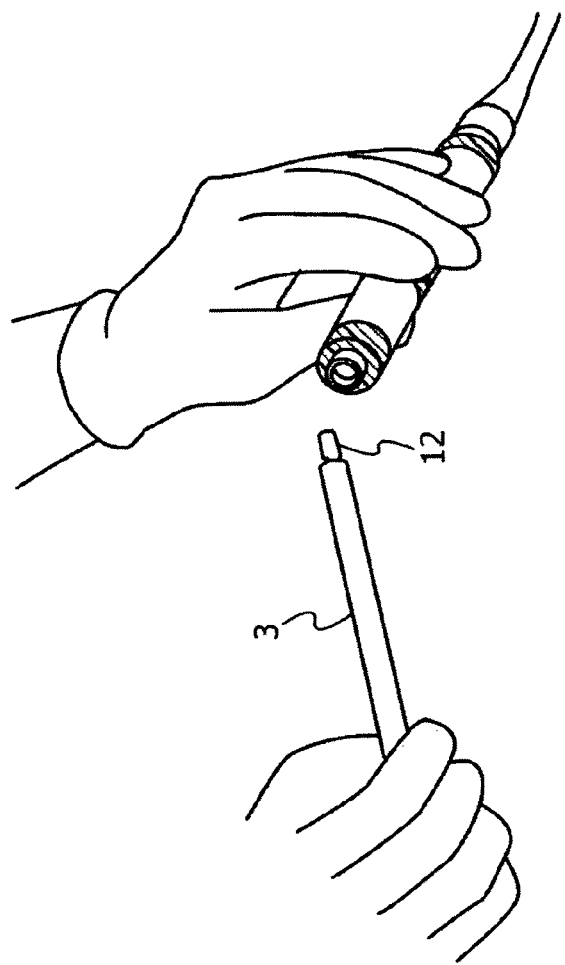
FIG. 6 shows a non-disposable camera head being loaded manually into a disposable endoscope housing.

Reference is first made to FIGS. 1A-1C which shows schematically the overall construction of one example of a semi-disposable endoscope. FIG. 1A is an overall view of the device, showing the non-disposable element 3, which generally contains the operating payload, in its internal chamber 10 of the endoscope. Propulsion of the endoscope is achieved by sequentially inflated annular balloons 4 mounted on the tubular outer body 7 of the endoscope. A window 1 in the endoscope head separates between the body fluids and the non-disposable element, thus keeping the element clean, and preventing contact between the non-sterilized operating payload 3 and the subject's body passage outside. The window 1 may be transparent, so that if the payload 3 is a camera, the optical port 2 has a clear view through the front of the endoscope. The non-disposable element 3 may be connected to the outside by an electrical and/or fluid line 6. Other alternative methods of transferring data to the outside and receiving instructions therefrom include a wireless link, or an on-board storage device, whose contents can be downloaded after removal of the payload. A working channel 5 may be provided to enable tools to be passed through the endoscope to the front of the head. The working channel 5 must be separate and isolated from the non-disposable element chamber 10, to avoid contamination of the non-disposable insert by the body fluids in the working channel.

FIG. 1B shows an end-on view of the endoscope, showing the end-seal 8, whose function is to isolate the non-disposable payload 3 from the bodily environment in which the endoscope is working. In this cap seal, there is seen a transparent window 1, an exit for the working channel 5, and additional holes 9, such as for providing irrigating water or inflation gas to the subject's bodily lumen. These channels run the full length of the endoscope and its multi-lumen tail, and their contents are isolated from the non-disposable element. Since the payload 3 is inserted from the proximal end of the endoscope chamber 10, the end seal 8 can be made as an integral part of the endoscope outer housing 4, 7, such that hermetic tightness is ensured. The optional balloon propulsion unit 4 can be seen surrounding the end seal.

FIG. 1C shows a method of insertion and extraction of the non-disposable element 3 into and out of the central chamber 10 of the disposable endoscope, from the back side of the endoscope, keeping the non-disposable element isolated from the subject's body.

Although the non-disposable element 3 is shown in FIGS. 1A and 1C, and in the following drawings also, as a long thin element, it is to be understood that it could be of much shorter length, and could also be of flexible form, such that it can negotiate any tight corners encountered in the passage being traversed.

Reference is now made to FIGS. 2A-2C which shows another method of assembly of such a semi-disposable endoscope, in which the non-disposable payload 3 is inserted from the distal end of the endoscope device into its chamber 11. The non-disposable element 3 may have an electrical and/or fluid connector 12 at its proximal end, which connects to a mating connector 13 within the disposable part of the endoscope, when the payload is inserted into its housing. The endoscope outer body may have a securing device for this part 13 of the connector, such as a step in its rear outer wall 7, to ensure that the payload makes good contact with the connector when it is pushed home. The non-disposable payload element 3 may then be sealed inside the central chamber 10 of the disposable outer housing by means of a sealing cap 8, such as is shown in FIG. 2B. This cap may be made of a flexible polymer material, so that when it is applied, it fits tightly over the front end of the internal chamber 11 in order to protect the non-disposable payload from the surrounding environment and to protect the surrounding bodily environment from possible contamination by the generally non-sterile payload. If the seal is not watertight, the non-disposable element may need to be disinfected between procedures because of possible contamination from its contact with the body fluids. The sealing cover should fit sufficiently well that even the nearby working channel 5 and supply channels 9 have no fluid connection with the payload enclosure 11. The sealing cap should have a transparent front window 1 if the payload is a camera head. FIG. 2C shows the method and directions of insertion of the payload 3. Further details of the method of use of this semi-disposable endoscope are given in relation to FIGS. 4-13 hereinbelow.

Additionally, since the non-disposable element 3 has to be retrieved from the proximal end, in those cases where data transfer to and from the head is provided wirelessly, or generated data is stored on-board, and there is therefore no need for an electric wire output connection 12, 13, 14, to the working station, it is still necessary to be able to withdraw the non-disposable element out of the proximal end of the endoscope tail tube 15, according to one of the aims of the present endoscope designs. In such examples, therefore, a passive cord or cable can be used for pulling the non-disposable element 3 rearwards, and for extracting it from the semi-disposable endoscope. This cord could either be constructed as a tail part of the non-disposable element, or it could be part of the disposable endoscope housing, and connection between it and the non-disposable element be made using a mechanical connector. Furthermore, a fluid transfer line such as a water or an air line could be used to pull the non-disposable element 3 from the rear of the endoscope.

Reference is now made to FIGS. 3A-3D which shows schematically another method of assembly and disassembly of such a semi-disposable endoscope, in which the non-disposable element 3 is inserted between the head and tail of the endoscope device. The disposable device can be separated into distal 15 and proximal 16 sections. The non-disposable element 3 is inserted into the distal section 15 which is then connected to the proximal section 16. The connection between these two sections should be hermetic to prevent ingress of bodily fluids during the endoscopic procedure which could contaminate the non-disposable element 3. Simultaneously with attachment of the distal and proximal sections of the endoscope, electrical (or fluid) connectors 12 and 13 are also mated. After the endoscopic procedure is completed, the sections 15, 16 are disconnected, as shown in FIG. 3C. In FIG. 3D, the non-disposable element 3 is shown being withdrawn proximally from the distal disposable part, which, if performed carefully, can avoid contact of the non-disposable insert 3 with the potentially contaminated distal section.

The above described examples have shown the non-disposable insert as being inserted into the disposable part of the endoscope axially, most conveniently from the distal front end, as shown in FIGS. 2A-2C. According to further variations of this exemplary endoscope, the non-disposable element 3 could be inserted into the distal end of the semi-disposable endoscope from an aperture in the side wall of the endoscope, instead of through an aperture in the end of the endoscope. In such a case, the sealing device will not be a cap, but rather a surface seal which renders the cover of the aperture sealed against ingression of fluids. Reference is now made to FIG. 3E, which illustrates insertion of the non-disposable insert into its distal enclosure 40, by means of an opening in the wall of the disposable part of the endoscope. The opening can be sealed by means of a side cover 41, which can be closed by swinging on a hinge, as shown in FIG. 3E, or by sliding shut. A seal has to be provided at the cover closure surface, to ensure isolation of the non-disposable insert. Side wall insertion of the non-disposable insert may require a comparatively short insert as is shown in FIG. 3E. The important feature of the endoscopes described according to these implementations of the present invention is that the non-disposable part installed in the distal portion of the disposable endoscope, whether through an axial entry aperture, or otherwise, is withdrawn from the proximal end after use, to avoid contact with any contaminated part of the endoscope.

In any of the above described exemplary semi-disposable endoscopes, the connector on the disposable element can be specifically designed for single use operation only, such as by ensuring that it is functionally destroyed when disconnected, so that re-use of the disposable element will not be possible.

In order to illustrate more clearly the advantages of the use of semi-disposable endoscopes as described in this application, reference is now made to FIGS. 4A to 13, which show suggested stages in the use of the exemplary device shown in FIGS. 2A-2C hereinabove. Of the three exemplary devices shown hereinabove, this form of the semi-disposable endoscope would appear to provide particularly good protection against cross contamination between the non-disposable payload of the endoscope and the disposable outer housing of the endoscope. The non disposable, multi-use element in the example shown in these drawings may be an endoscope camera, which, because of its expense, is not disposable, and therefore cannot be simply discarded after use. However, sterilization of the camera and cleaning it after use is problematic, such that it should be protected from all contact with the bodily passage in which the endoscope is operating. Although these endoscopes are described in terms of the use of an endoscope camera head as the non-disposable, it is to be understood that the claimed invention is not meant to be limited to such a camera head, but is applicable for use with any other tool that needs to be isolated from the bodily passage environment.

FIG. 4A shows schematically an exemplary disposable endoscope housing, which can optionally include a propulsion head using locomotion balloons 4, or another form of propulsion, or it can be non-propelled and pushed in from the rear. The viewing port 2 of the non-disposable camera is shown at the front end of the endoscope, with the sealing cap 8 positioned in front of it showing how it is applied once the camera has been installed. The disposable section also includes the endoscope tail 15 which may incorporate multiple lumens for inflation, tool introduction, water, gases, etc, as well as the electrical leads 14 to the non-disposable element in the endoscope head.

Reference is now made to FIG. 4B which shows schematically a non-disposable camera head 3, with its feed electric cable 14, which may be detachably connected to the camera head 3 by means of an electrical connector 12, 13. The cable 14 and its associated connector part 13 are generally mounted within the disposable endoscope tail lumen 15, with the electric cable 14 spanning back from this point to the proximal entry point of the endoscope tail lumen. As seen in FIG. 4A, the transition section 16 between the tail lumen 15 and the endoscope head may be so shaped as to conform to the shape of the connector part 13, Typically, the cable has a female socket 13, while the camera has a male plug 12, though the reverse is equally applicable. In this application, the preferred embodiments are shown as having a male connector on the non-disposable, and a female connector within the endoscope on the distal end of the cable. The connector may have an auto-locking function, so that the mated connector cannot be inadvertently released during the endoscopic or withdrawal procedures. Furthermore, the connector part in the disposable multi-lumen cable outer sheath 15 may be of a single use type, which is functionally destroyed on mating or disconnecting, so that it cannot be used more than once. The connector part 13 attached to the cable 14 may advantageously have a "torpedo shape", tapered towards its rear end, to enable easy withdrawal back through the multi-lumen cable outer sheath 15, when the procedure is completed. Additionally, the transition region 16 between the body of the endoscope and the multi-lumen tail 15 may also have a tapered form, as shown in FIG. 4A. This shape has the dual purpose of enabling easier withdrawal in the proximal direction of the entire semi-disposable endoscope after the procedure, and of enabling easier withdrawal in the proximal direction of the non-disposable camera from the disposable endoscope, once the endoscope has been removed from the subject. This withdrawal is generally performed with the camera head attached to the connector, and its function will be further expounded hereinbelow.

The non-disposable insert 3 may also contain other multiuse devices, in addition or besides the camera head. Some such possible devices are shown in FIG. 4B. In the example shown in FIG. 4B, the camera head 24 is shown equipped with illuminating sources 30, such as LED's, to illuminate the region immediately preceding the front window, so that the camera can image the region. Additional elements shown within the non-disposable housing include electric motors 25, 26, to provide controlled steering to the endoscope head, and an electronic unit 27, which can be used for processing the information provided by the camera, or for control of the illumination or steering of the endoscope, or for other functional operations. This unit can also possibly incorporate an on-board battery for powering the various endoscope electronic functions. Additionally, electronic, magnetic or ultrasound probes or sensors, a spectral analyzer, or similar such units may be carried in the non-disposable head.

The embodiment described in FIGS. 4A-4B, and the continuation Figs. below, utilize a camera head 3 which is attached by means of a detachable connector to an electrical cable 14 which remains in the endoscope. The cable 14 is then regarded as a disposable part. This is a particularly convenient arrangement since only the camera head 3 itself then needs be slid into the endoscope housing, to mate with the cable already installed. However, it is to be understood that the invention will also operate, though perhaps less conveniently, if the cable is attached to the camera as part of the non-disposable, and is threaded into the endoscope before the procedure.

Figure 5:
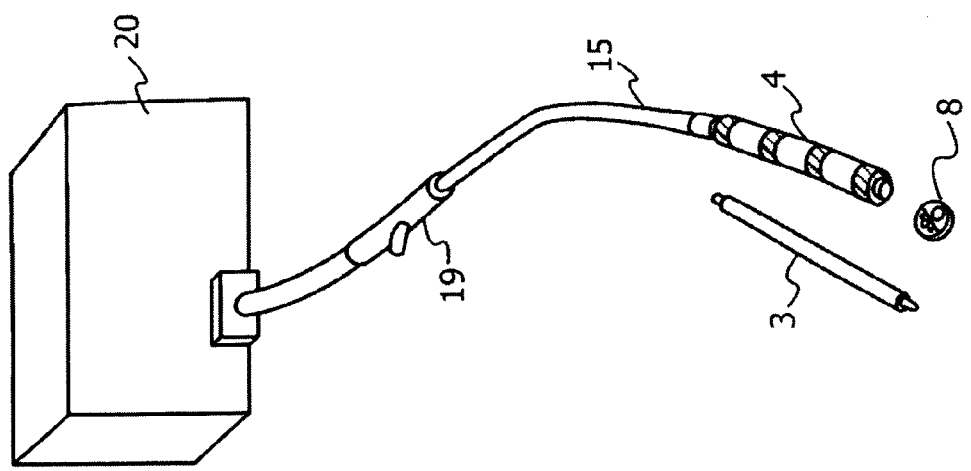
FIG. 5 is a schematic illustration of a complete endoscopic device before the non-disposable camera is inserted into the disposable housing.

Reference is now made to FIG. 5 which is a schematic illustration of the entire endoscope device before the non-disposable camera 3 is inserted into the disposable endoscope 4. The end cover seal 8 is also shown ready for sealing the camera 3 into the disposable endoscope housing 4. The disposable endoscope is shown in FIG. 5 attached to its working station 20 by means of a tail lumen 15, which can be multi functional. The tail lumen 15 may incorporate a access port 19 so that biopsy forceps, or another surgical tool may be inserted into the endoscope down the working channel.

The working station may supply at least some of:
(a) Air pressure for balloon locomotion, if fitted.
(b) Electrical communication to and from the camera, and illumination and steering control.
(c) Suction
(d) Water for rinsing the camera cover
(e) Air for inflation of the bodily passageway, such as the colon, during the endoscopy.

Reference is now made to FIG. 6, which shows the non-disposable camera head 3 being loaded manually into the disposable endoscope housing. The connector 12 at the rear end of the camera head may be of a barbed or similar design to enable it to click into its matching connector or into a matching base in the disposable endoscope housing.

Figure 7:
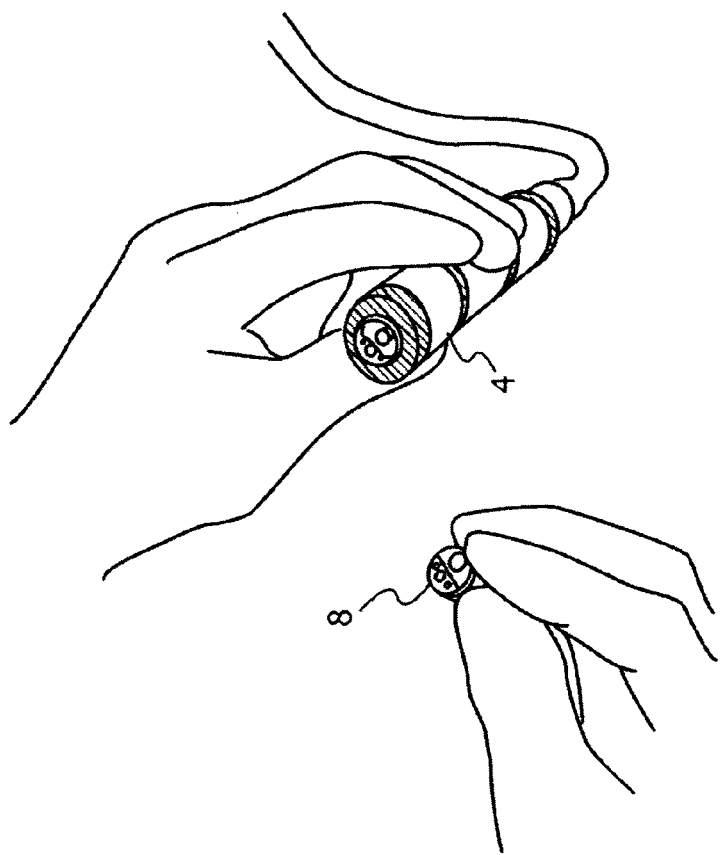
FIG. 7 shows schematically the capping of the endoscope after insertion of the camera.

Reference is now made to FIG. 7 which shows the capping of the endoscope. Once the camera head is clicked into place, the camera cover seal 8 is mounted on the front of the endoscope, ensuring a waterproof seal between the disposable endoscope 4 and the camera 3.

Figure 8:
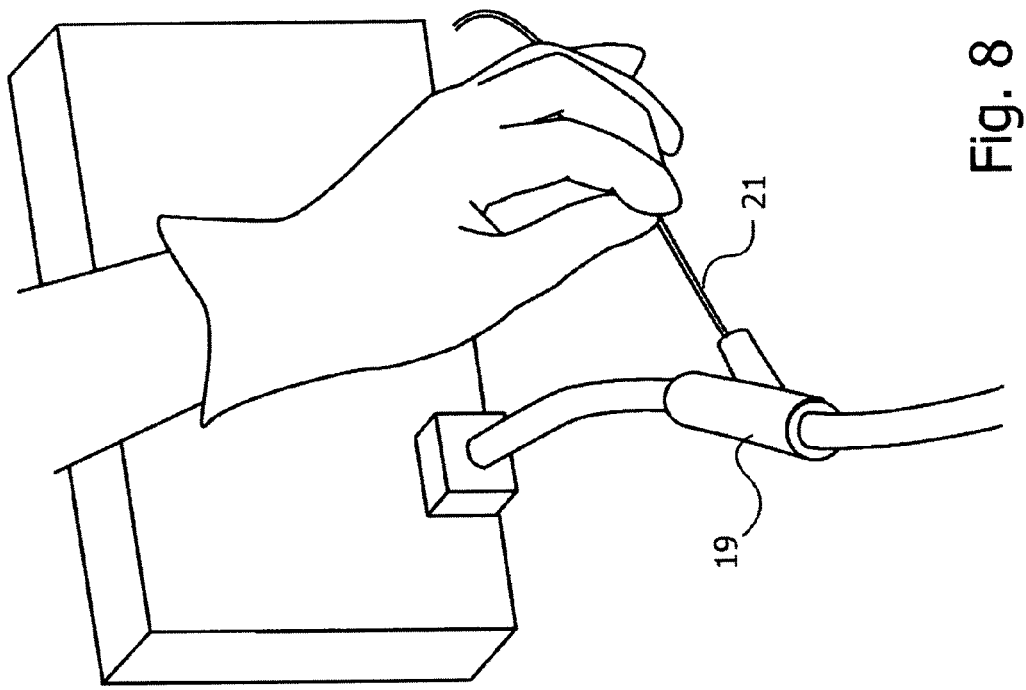
FIGS. 8 and 9 now show the method of use of a set of biopsy forceps with the semi disposable endoscope described in the previous figures.
Figure 9:
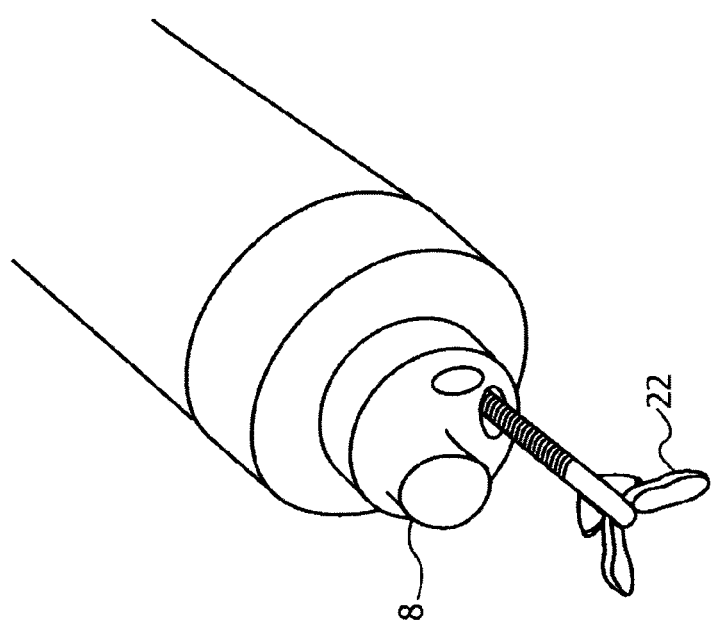

Reference is now made to FIGS. 8 and 9 which show an example of a method of use of the semi disposable endoscope described hereinabove. FIG. 8 shows the threading of the operating cable 21 of a set of biopsy forceps down the access port 19 of the endoscope and into the working channel. FIG. 9 is a schematic close-up view of the distal end of the endoscope, showing the sealing cap 8 with the jaws 22 of the biopsy forceps projecting through the working channel hole in the sealing cap, and ready to take a tissue sample.

Figure 10:
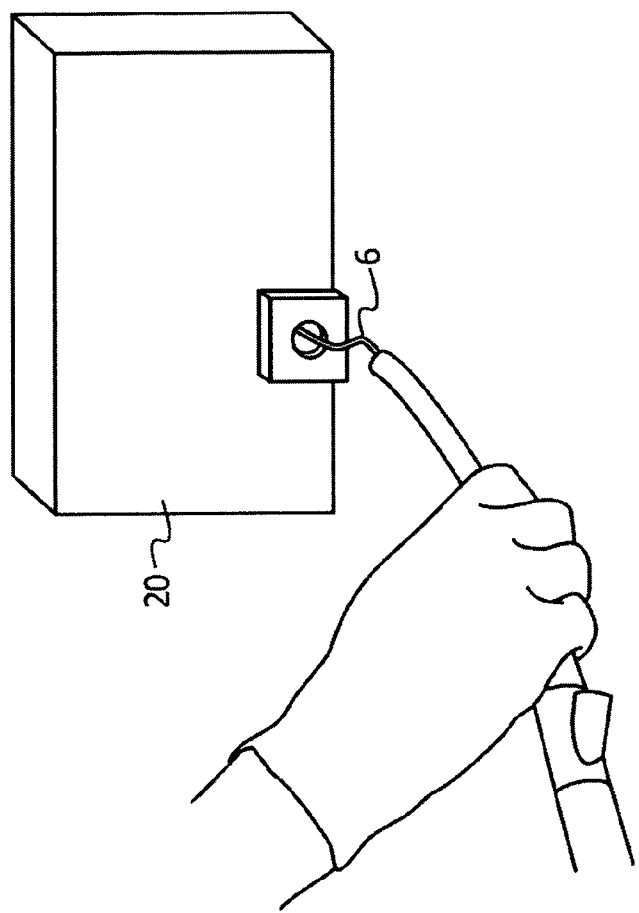

Reference is now made to FIGS. 10 to 13, which show novel methods of dismounting a semi-disposable endoscope of the type described in this application, and removal of the non-disposable camera head from within it in a manner such that contamination of the non-disposable camera head by contact with the outer surface of the used endoscope is prevented during the withdrawal process. This novel feature of the endoscopes described in this application enables the non-disposable camera to be repeatedly used without the need for a full sterilization between successive procedures, thus contributing to the advantages of the semi-disposable endoscopes described herewithin. FIG. 10 shows the physician removing the endoscope from the workstation 20, after the endoscope has been removed from the patient's body. The electrical cable 6 is visible after detaching the endoscope from the workstation, such that the cable 6 can then be pulled out through the back of the tail lumen 15 of the endoscope, as shown in FIG. 11. According to an alternative removal procedure, the endoscope connection port of the workstation can be constructed such that the electrical cable can be pulled into the working station without the need to detach the endoscope. As the cable 6 is pulled in the proximal direction, it pulls the non-disposable camera 3 with it back out of the tail lumen. This is shown schematically in FIG. 12, where the camera 3 can be seen within the tail lumen 15 of the disposable endoscope. The endoscope tail 15 is generally of smaller diameter then the non-disposable element, since it must be flexible enough to negotiate sharp turns within the subject's bodily passages. It is therefore preferably constructed of a radially flexible material, expanding as the non-disposable 3 is being pulled through it. Finally, as shown in FIG. 13, the non-disposable camera 3 is seen exiting the endoscope body 15. Thus, the non-disposable has been successfully withdrawn from the disposable endoscope contaminated during its use, but without it having come into any contact with the contaminated outer surface of the endoscope.

The non-disposable camera head can then be detached from the electrical connector, such that it can be made ready for the next procedure, without the need for sterilization because of contamination from the previous procedure, and without the fear of contaminating the next procedure because of its unsterilized condition.

Reference is now made to FIGS. 14 and 15, which illustrate schematically cut-away views of an example of a semi-disposable endoscope such as those described in this disclosure, to illustrate a suggested internal structure thereof. In FIG. 14, there is shown a cut-away view of the distal end of an endoscope, showing a non-disposable camera head 3 in position within its enclosure in the endoscope housing, and a working channel 18 located beneath the camera enclosure, and isolated therefrom. The end cap 8, with its transparent window 1, seals the camera bay from the outside environment. A connector 12 in the base of the camera may be mated with the corresponding connector socket 13, disposed at the transition between the endoscope head and the tail 15. In FIG. 15, there is shown a cut-away view of the proximal end of this endoscope, showing a port block 18, for mounting the endoscope to the work station, and an access port 19 to the working channel, to show how a tool such as a set of biopsy forceps can be inserted into the working channel.

The disposable endoscope and its cap may generally be supplied in a sealed, sterile, single-use package. The camera head, on the other hand, is generally supplied in a clean, but generally non-sterile, condition. Use of some of the examples of semi-disposable endoscopes described in FIGS. 1 to 15 of the present application, and especially the exemplary endoscope shown in FIGS. 2A-2C and corresponding drawings, thus enable a non-sterile, non-disposable element such as a camera head, to be inserted into the front end of the disposable endoscope without causing contamination of the sterile endoscope. Additionally, after use of the endoscope, at which point the endoscope will generally be contaminated from contact with the subject's body fluids, use of such endoscopes enable the non-disposable element to be withdrawn from the rear end of the endoscope, which is generally not contaminated, without contamination of the non-disposable by the used endoscope.

In the above described examples of the use of the semi-disposable endoscopes of the present disclosure having distal loading of the non-disposable element, the assembly of the endoscope—namely, insertion of the non-disposable camera unit and its sealing using the cap—is shown being performed manually by the technician or the physician using the endoscope, as in FIGS. 6 and 7. According to further examples of the implementation and use of the semi-disposable endoscopes shown in the present disclosure, there is described hereinbelow, a kit and method for supplying all of the disposable parts of such an endoscope in a sterile form, and for assembling the complete endoscope with minimal use of manual manipulation and with minimal risk of contamination of the endoscope before use.

Figure 16:
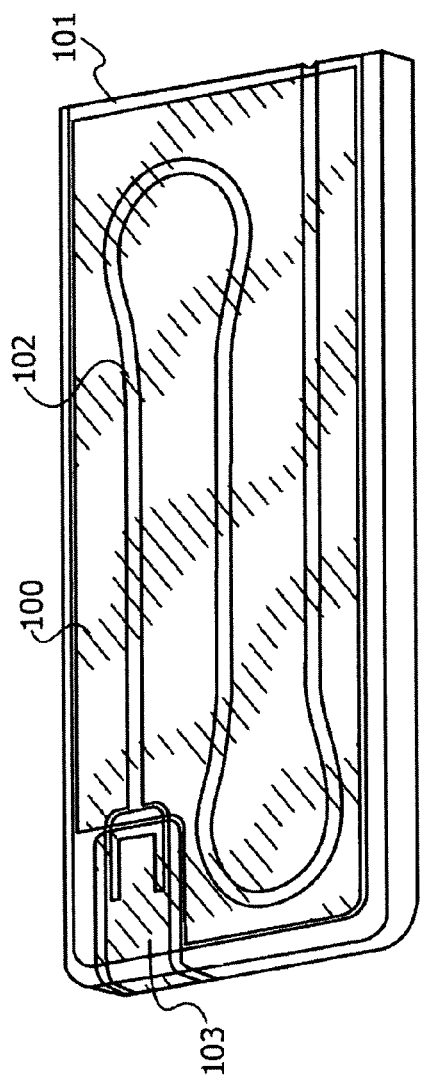
FIG. 16 shows a sterile supply tray for dispensing the disposable parts of the endoscope, namely, the endoscope body and the camera cover cap.

Reference is now made to FIG. 16, which shows an example according to another aspect of the present invention, of the packaging of the endoscope and its cap in a single-use tray, in a manner which will enable optimal use of the above advantages of these endoscopes. The disposable part of the endoscope may be advantageously supplied wrapped in a sterile package together with the cap. The cap is mounted in a novel dispenser that enables it to be applied to the disposable endoscope without manual handling. The packing may be such that only the opening for the camera is exposed when the first stage of the package opening is performed, allowing the technician or physician to insert the non-sterile non-disposable camera into the housing, and then to close the housing with the sterile cap. The technician or physician is thus presented with the sterile disposable parts in such a manner that they can be used without danger of cross contamination from the generally non-sterile camera head. By this means, when the remainder of the packing is removed, only sterile surfaces will be exposed, the non-sterile camera being isolated within its enclosure within the sterile housing.

FIG. 16 shows a sterile supply tray 101 onto which are packed the disposable parts of the endoscope, namely, the long endoscope body 102, shown for simplicity in this example without a locomotion unit, and the camera cover cap. Each of these two parts may be packed under separate protective coverings 100, 103, which can be removed independently of each other. The coverings may be of a transparent plastic film, so that the contents of the tray can be examined or identified before opening. The camera cover cap is packed mounted in a special dispenser, whose operation will be described in more detail below, and which enables the user to mount the cap on the endoscope body, after the camera has been inserted, without compromising the sterility of the cap by contact with the camera head.

Figure 17:
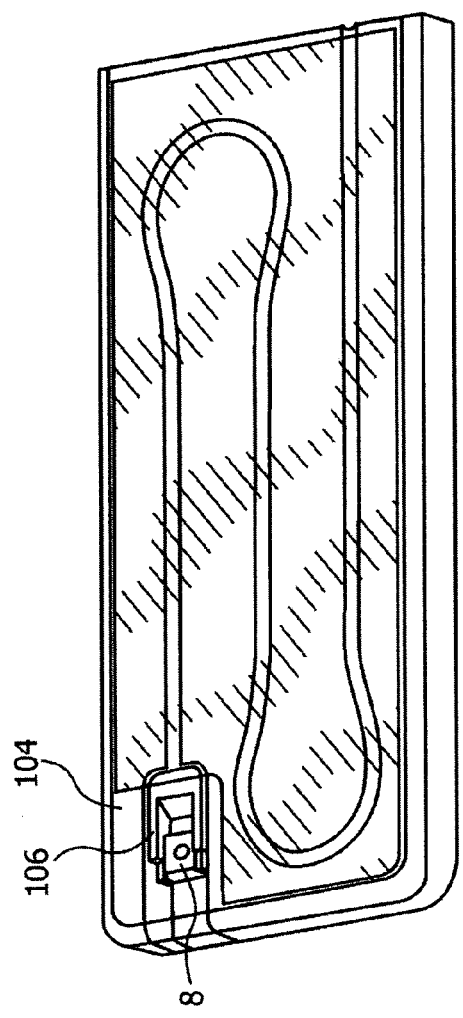
FIG. 17 shows the tray of FIG. 16 after removal of part of the protective covering, revealing the sterile cap mounted in its sterile dispenser.

Reference is now made to FIG. 17, which shows the tray after removal of the protective covering 104 of the cap dispenser 106, revealing the sterile cap 8 mounted in the sterile dispenser 106. The film is still shown in position over the rest of the tray, protecting the endoscope body from contamination.

Reference is now made to FIGS. 18 to 22, which show an example of the detailed operation of such a cap dispenser. For simplicity and to show the details of the procedure, these drawings show a blown-up, cut-away view only of the cap dispenser separate from the tray, although the dispenser is advantageously built into the tray, as shown in FIGS. 16 and 17.

Figure 18:
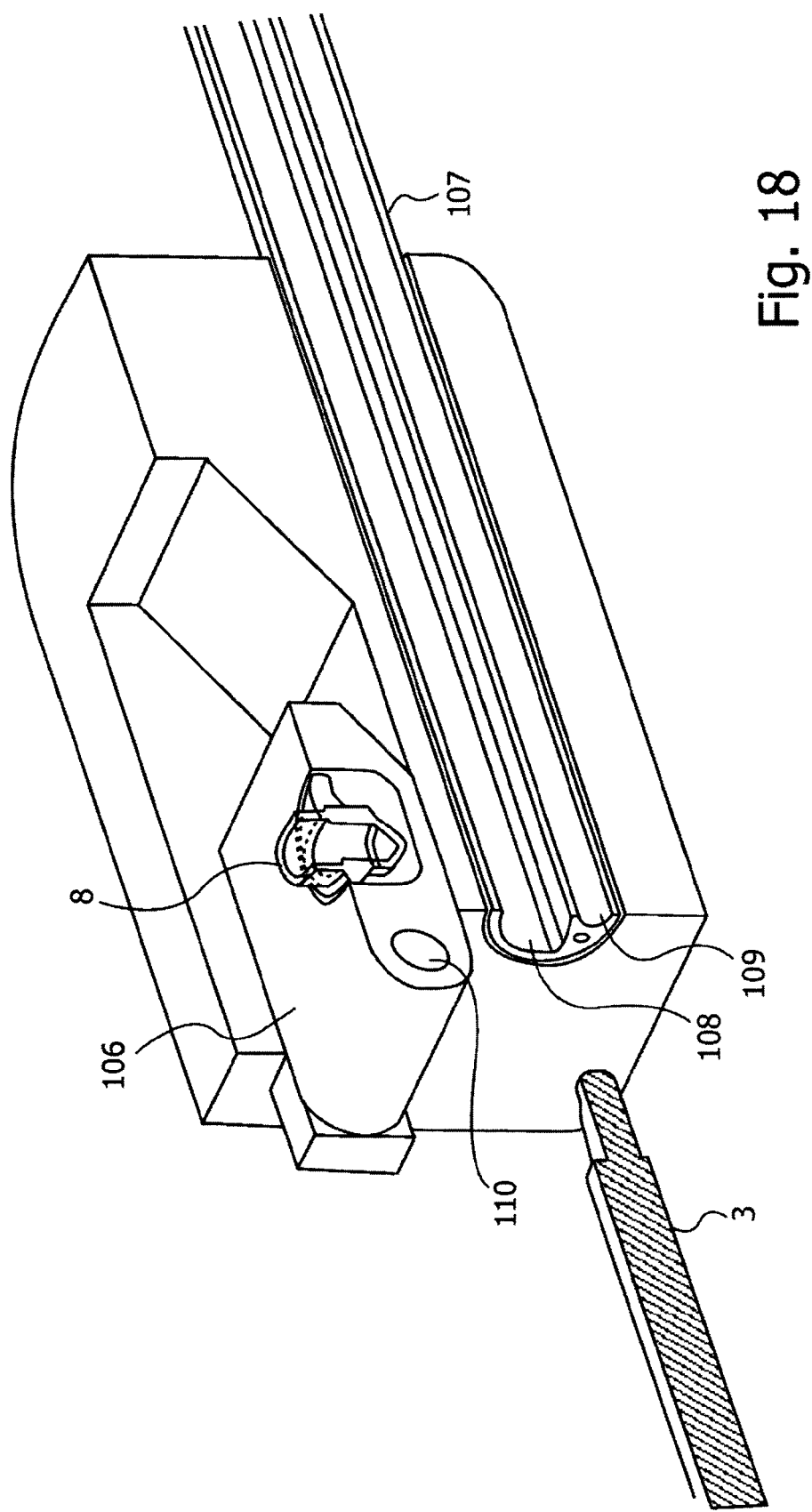
FIGS. 18 to 22 show details of the operation of the cap dispenser of FIG. 17, illustrating the cap's application to seal the non-disposable camera into the disposable endoscope body.

In FIG. 18, the cap dispenser 106 is shown with the cap 8 mounted in it. The cap dispenser is mounted to the tray by means of a pin or axle 110, enabling the cap dispenser to rotate about this axis. The disposable endoscope body 107 is shown within the groove of the tray, with only the distal front surface exposed. In this front surface, the opening 108 of the camera bay for receiving the camera 3 can be seen, together with the exit of the working channel 109. The non-disposable camera head 3 is shown on the left hand side of the drawing, ready for insertion.

Figure 19:
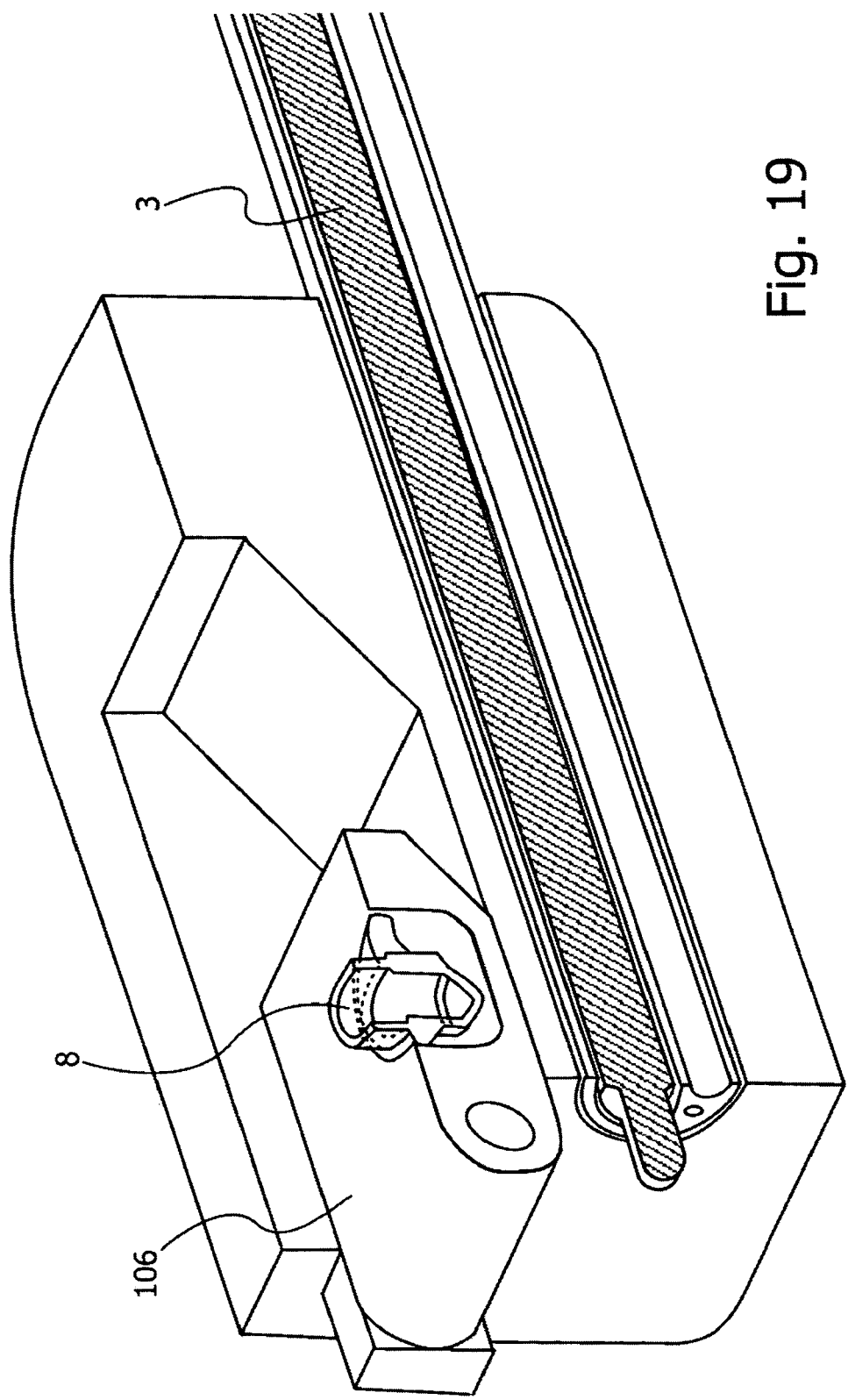

In FIG. 19, the non-disposable camera 3 has been inserted into its enclosure into its correctly deployed position. One aspect of the present invention which should now become clear is that the only contact which the non-sterile camera has with the sterile endoscope is at this distal front surface, which will soon be covered by the camera cover cap. This ensures that even if that front edge of the camera bay did become contaminated by the camera, it too, like the camera, will be isolated within the sterile disposable endoscope part, once the sterile cap has been fully applied.

Figure 20:
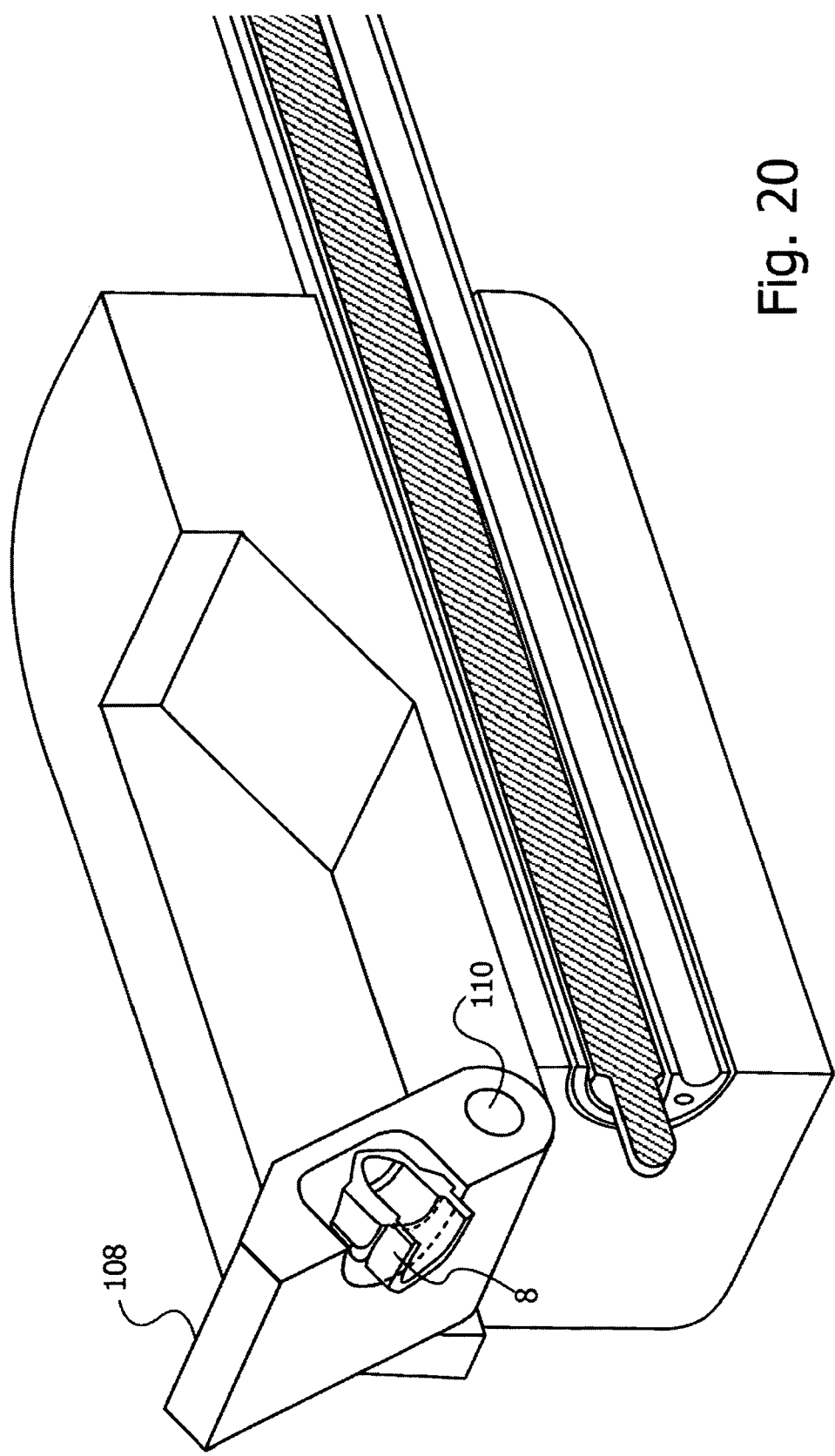
Figure 21:
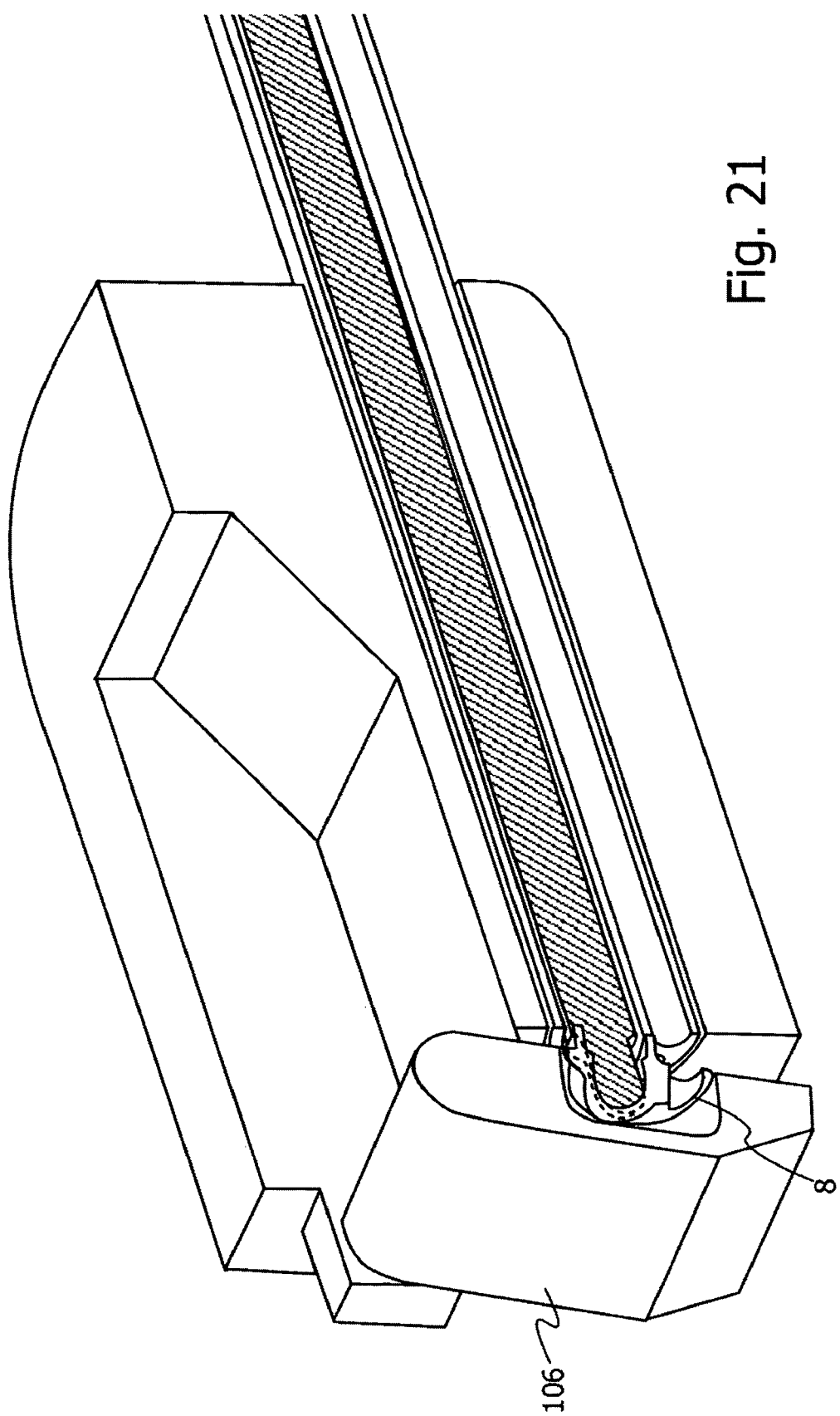

Reference is now made to FIG. 20, which shows the hinged dispenser arm containing the cover cap 8 being rotated by on its axis 110, thus bringing the cover cap 8 into the correct closure position for sealing the camera head 3 into the disposable endoscope, as shown in FIG. 21.

Figure 22:
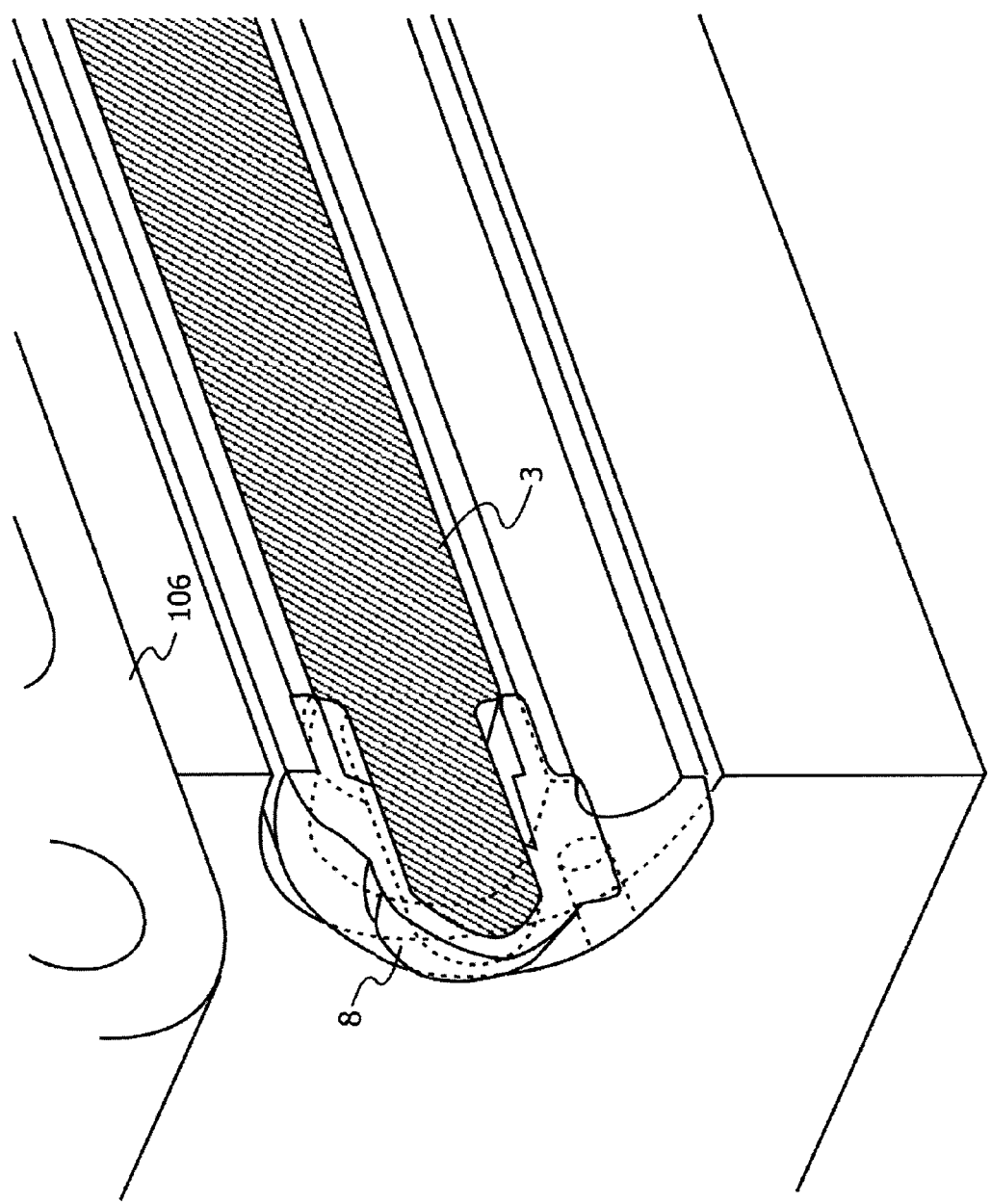

FIG. 22 shows how, once the cover cap 8 is firmly in place, the hinged dispenser arm 106 can be swung back out of the way. FIG. 22 also shows a close-up view of the cover cap 8 firmly in place, sealing the camera head into its enclosure in the endoscope body. The working channel is clearly seen below the camera head enclosure, and the cap should have openings opposite the working channel to provide access for any surgical implements and for water or air supplies where appropriate.

Figure 23:
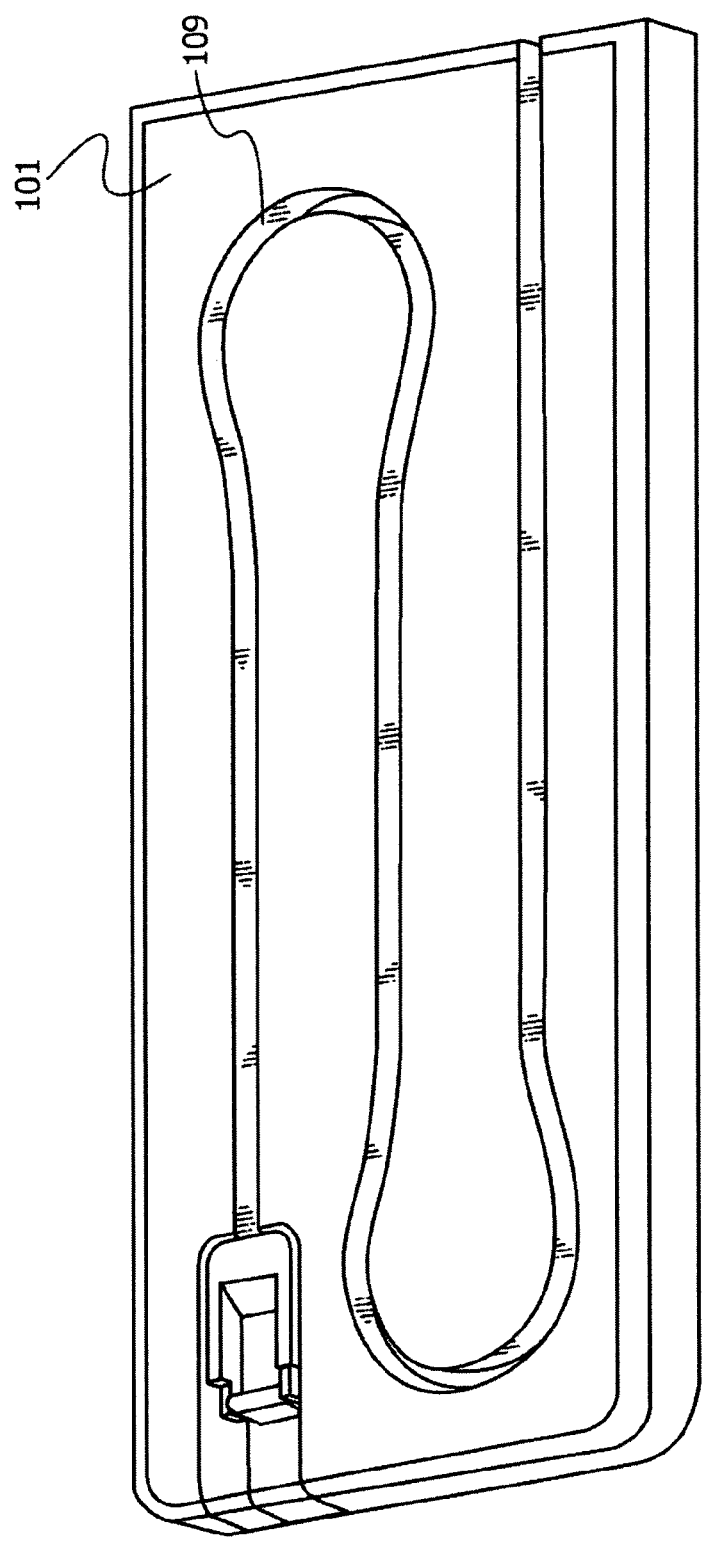
FIG. 23 shows the supply tray after the sterile endoscope has been capped and removed for use.

Once the camera head has been installed and sealed by the cover cap, the remainder of the sterility protection wrapping of the tray shown in FIGS. 16 and 17, which protected the endoscope while the camera head was being inserted, may now be removed, and the sterile endoscope removed from the tray for use, leaving the empty tray and used cap dispenser, as shown in FIG. 23.

Reference is now made to FIGS. 24A to 24G, which illustrate further examples of inflated balloon endoscopes generally having auto-inflation propulsion, and adapted for providing navigational abilities to enable the endoscopes to negotiate curved passages, such as are encountered in colonoscopic applications. It is to be understood though that these devices are not meant to be limited only to colonoscopic applications. In order to fully operate the endoscope and to have full access to the inner side of the lumen, such as for removing polyps, steering in four directions—up, down, right and left—is required, including combinations thereof. In prior art endoscopes, this is usually achieved by means of cables connected to the head unit and running all the way rearwards through the endoscope to the working station. At the tail section, steering wheels are usually provided for pulling the wires.

Referring now to FIG. 24A, there is shown a schematic view of a non-disposable element of the type shown in FIG. 4B, incorporating a set of electrical actuators or motors for steering the front tip of the endoscope. The non-disposable element may comprise the following sections: a head section 20 incorporating a camera and illumination, a steering section 21, digital processing and/or an optional battery section 22, and the tail connection section 23, as described in the previously described endoscope examples. In the presently proposed example, the steering wires are pulled from inside the endoscope by means of electrical actuators, for example electrical motors with pulleys, or lead screws, or linear actuators. Consequently, no steering wires have to be passed outside the body. Control wires 29 run down the length of the non-disposable element for receiving the power and for transmitting control instructions to the electric motors. Alternatively, the control instructions can be transmitted wirelessly, and/or the power be derived from an on-board battery. Cross sectional views of the non-disposable element at various points down its length, are shown in FIGS. 24B to 24E, to illustrate the positions of the motors and steering wires.

In the example shown in FIG. 24A, two electrical motors 25, 26, are shown. Their activation results in the pulling of wires 25A and 26A respectively. These wires are attached at their ends remote from the motors to anchor points 30 in the head section 20, causing it to bend, as shown in FIG. 24B. In the cross sectional view of the element shown in FIG. 24C, are shown the positions of the four wires that enable achievement of the required four directions of steering. In FIG. 24A, the steering wires 25A and 26A are shown in the plane of the drawing. The front motor 25 has to be of reduced diameter such that the wires 26A from the rear motor 26 can pass the motor 25. In the cross section of FIG. 24C, the wires 25A and 26A are shown orthogonal. The steering wires are contained within a flexible housing 31. Section 31 is constructed of a material which resists compression, but allows flexion. Alternatively, the steering wires can be made sufficiently rigid that they can also support compressive forces, in which case only two wires, preferable located in sectors at 90 degrees to each other, can be used for achieving the desired four directions of movement.

The motors and the wires are all located inside the flexible body as shown in FIGS. 24F and 24G. The bending in section 38 arises from the flexibility of the non-disposable element 31 body as it passes through the lumen it is traversing, and not because of actual steering by actuators. FIG. 24H shows the steering generated by the electrical actuators, which all takes place in this exemplary device, within flexible section 31.

This exemplary implementation is not limited to the four directions of actuation. Additional actuators can be used in the similar way to achieve more degrees of freedom: forward-backward, twisting along the endoscope axis. Thus, for instance, the use of at least three motors with two wires from each, such that there are six wires most conveniently oriented at nominally 60° to each other, enables rotation of the endoscope head to be achieved. Another method of achieving rotation is by using at least one motor designed to rotate on its own axis, in addition to pushing or pulling on its wires. Alternatively, the wire anchor points 30 can be mounted on a rotatable element instead of being fixed, such that rotation of the head is achieved.

It was shown in the exemplary semi-disposable endoscopes shown in FIGS. 1A-3C that the non-disposable element is connected to the disposable element and is parallel to the working channel. Thus, bending of the non-disposable element causes bending of the working channel, which enables pointing of the endoscope tip to a region of interest.

It is to be understood that other types of actuation besides electrical actuation may equally well be used—pneumatic, electrostatic, magnetic, or the like.

The non-disposable element in FIG. 24G may be constructed to have the ability to stiffen on demand by the use of electrical, pneumatic or mechanical actuators. The steering wires can be made non compressible, such that locking the motors will lock the shape of the non-disposable element. This may be a useful feature for fixing the endoscope position after pointing the head to remove a polyps or to examine a region of interest.

The non-disposable element with camera and steering can be controlled by wires that go through the length of the disposable element lumen. This requires two electrical connectors 12, 13 for connecting the non-disposable device to the working station. Alternatively, the non-disposable components can be controlled wirelessly. The camera sends images or streaming video preferably by radio-frequency (RF) transmission, and the motors can also receive commands from the control pad or working station by RF. If a battery too is located on the non-disposable part, then there is no need for any electrical wires coming from the non-disposable element, which simplifies the disposable element. The battery can be charged wirelessly by placing it into wireless charger, such as operated by an alternating magnetic field. The battery can also be charged through a connector, in which case there is a need for an electrical connector on the non-disposable device.

In order to traverse smoothly inside a body lumen, such as the colon, the front section of the endoscope needs to conform to the geometry of the lumen, and should not have any sharp or small elements. Reference is now made to FIGS. 25A-25C, which illustrate schematically, another exemplary aspect of the present invention, for providing self-navigating properties to an endoscope. The endoscope shown in FIG. 25 has inflatable balloon type of propulsion, such as described in the above mentioned published PCT Application WO 2007/017876. Sequentially inflated balloons 55, 54, 53 provide the propulsion for motion through the lumen 50. The endoscope of FIG. 25A differs from those shown in the prior art by the addition of a self-navigating inflatable balloon 51, which can be conveniently inflated by a separate inflation pipe 52. FIG. 25B illustrates how the guidance balloon steers the main balloon propulsion unit into a curve or bend in the lumen being negotiated. When the endoscope reaches the bend, by inflating the guidance balloon 51, its contact with the outer edge of the bend pushes the head into the direction of the bend, and helps to steer the endoscope to the enter the bend correctly. The guidance balloon 51 preferably has an annular form, as shown in FIG. 25C, thus enabling the non-disposable element to protrude through it and have a clear forward view 57. This forward view can be used, in addition to its usual functions of inspection, for providing the system with feedback about the curvature of the lumen immediately ahead of the endoscope tip, such that with suitable feedback control, the inflatable tip balloon can be self navigating.

The internal pressure, which defines the level of stiffness or the size of the balloon 51 can be changed and controlled from outside, depending on the requirements. If for example the lumen gets wider, the balloon can be inflated more, and if narrower, it can be inflated less. If the balloon is constructed of a material having low-compliance, the pressure in it will change the stiffness of the balloon which can assist the endoscope tip in negotiating sharp turns, such as occur in the human colon. The balloon pressure can be sampled from outside to provide data and safety in use.

Although this example has been described for use with a sequentially inflated balloon type of propulsion, since in such an application, the means of providing inflation fluid are already present, it is to be understood that it is not limited thereto, but can be used for other types of self propelled endoscope. Its use in endoscopes advanced manually can also be envisaged, on condition that the inflatable guidance balloon is used in conjunction with careful visual control, and co-ordination of the insertion force and the inflation balloon functioning.

Reference is now made to FIGS. 26A and 26B to illustrate schematically more examples of inflatable chamber locomotion mechanisms for endoscopes, using orifice flow control to manage the inflation and deflation of the balloons. FIG. 26A shows the use of active control, while FIG. 26B shows control by the use of one-way valves.

FIG. 26A shows an endoscope propulsion system utilizing multiple annular balloons 62, 63. Sequential balloons are connected and fed by orifice sections 60A, 60B, 60C, containing orifices 67, 68B and 69B. In published PCT application WO2007/017876, and in PCT Application Nos. PCT/IL2008/000180 and PCT/IL2008/000173, the orifices are described as being always in an open state, and the sequential inflation is ensured by the dynamics of the fluid flow through the orifices and into the successive elastic balloons. In the exemplary propulsion unit shown in FIG. 26A, the orifices are equipped with electrically operated valves 68C, 69C that can open and close, thus controlling the flow through the orifices. In this endoscope, the dynamics of the flow can be controlled by the electrical valves, while still using the advantage of a single supply line 64. The valves may be actuated by electrical signals provided by a control wire 70. Valve 68C is shown in its open state, while valve 69C is shown in its closed state. The control unit with the power source can be located either on the device or externally.

FIG. 26B shows another exemplary endoscope propulsion system utilizing multiple annular balloons 71, 72, 73, in which the sequential opening of the orifices 81A, 82A, is achieved in an automatic manner by use of one-way, pressure activated valves. Valves 81B and 81C are one way valves that control the flow through orifices 81A between adjacent balloons 71 and 72. Likewise, valves 82B and 82C are one way valves that control the flow through orifices 82A between adjacent balloons 72 and 73. The valves open when a predetermined pressure difference is established between the adjacent balloons. When a valve opens, it stays open until a flow in the reverse direction is established. For a valve opening with an inflation flow of fluid, a back flow will be detected only when the entire series of balloons is full, and that the deflation cycle has begun. When such a valve detects a back flow, it changes its state to closed, closing off the orifice. The reverse procedure occurs for a valve opening with an deflation flow of fluid. Each transition between adjacent balloons has at least a pair of oppositely facing valves, namely valves 81B, 81C for orifices 81A, and valves 82B, 82C for orifices 82A. The opening of each one of a pair of valves is controlled by the pressure difference generated in opposite directions.

Referring again to FIG. 26B, the inflation sequence takes place as follows:
1. Initial status:
(a) All the balloons 71, 72, 73 are empty.
(b) All the valves 81b, 81C and 82B, 82C are closed.
2. Inflation phase:
(a) Fluid is filled via supply line 64 and orifice 80A.
(b) Balloon 71 begins to inflate and when the pressure difference between balloons 71 and 72 becomes sufficiently high, one way valve 81C opens and locks itself in an open position. (This open position is maintained until it detects a reverse pressure difference, meaning that flow has begun in the opposite direction.)
(c) The fluid then flows through the valve 81C unimpeded, and balloon 72 begins filling.
(d) In the same way, the valve 82C of the next orifice opens when the balloon 72 reaches the appropriate pressure difference above that in balloon 73.
(e) All balloons thus become inflated.
3. Deflation phase:
(a) Fluid is allowed to escape via supply line 64 and orifice 80A, deflating the first balloon 71.
(b) When the fluid starts to leave balloon 71, the pressure difference between balloons 72 and 71 forces valve 81C to close and thus to shut off the orifice 81A.
(c) Now both valves 81B and 81C are closed.
(d) The resulting difference of pressure between balloons 72 and 71 causes valve 81B to open and to lock itself in an open position, enabling flow of air from balloon 72 to 71 and to the discharge pipe 64.
(e) The flow continues sequentially until all balloons are empty, at which point:
4. The inflation phase starting again.
(a) When the inflation begins again, the valves 81B and 82B close because of the now forwardly directed pressure difference, and the situation described in paragraph 1 above has been reached again.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A device for insertion into a subject, comprising:
an elongate housing having a compartment at its distal end, said compartment having a sealable entrance aperture at its distal end and a first connector part disposed at its proximal end;
a connecting link attached to said first connector part and running proximally down said elongate housing;
an element adapted to be inserted into said compartment through said entrance aperture, said element having a second connector part which mates with said first connector part when said element is fully inserted into said compartment; and
a seal for sealing said compartment, such that after said element is inserted into said compartment, application of said seal provides isolation between said element and the environment outside said distal end of said device.

2. A device according to claim 1, wherein said connecting link is either one of an electric cable, a mechanical cord and a fluid conveying tube.

3. A device according to claim 1, wherein said connector parts are such that said element can be withdrawn proximally from said compartment by pulling on said connecting link.

4. A device according to claim 1, wherein said element is adapted for multiple use, and said elongate housing is adapted for a single-use.

5. A device according to claim 1, wherein said compartment, when sealed, isolates said element from the environment outside of said device.

6. A device according to claim 1, wherein said element can be used in a non-sterile condition in said device without generating contamination outside said device.

7. A device according to claim 1, wherein said elongate housing is constructed such that said element can be withdrawn proximally from said elongate housing without making contact with that part of the outer surface of said elongate housing which has been inserted into said subject.

8. A device according to claim 1, wherein said element comprises at least one of a camera head, a steering mechanism, an electronic, magnetic or ultrasound probe or sensor, and a spectral analyzer.

9. A device according to claim 1, further comprising at least one channel running through said elongate housing, said at least one channel being isolated from said compartment.

10. A method of using a device for insertion into a subject, comprising:
providing a device having a compartment with a sealable entrance aperture at its distal end and a first connector part at its proximal end;
inserting into said compartment, an element having a second connector part which mates with said first connector part when said element is fully inserted into said compartment;
sealing said entrance aperture;
performing a procedure on the subject; and
withdrawing said element from the proximal end of said device, such that said element does not contact those parts of the device that were in contact with tissues of the subject during said procedure.

11. A method according to claim 10, wherein said lack of contact of said element with those parts of the device that were in contact with tissues of the subject enables said withdrawn element to be inserted into another such device, without the need for sterilizing.

12. A method according to claim 10, wherein said first connector part has a connecting link attached thereto, said link being threaded proximally down said device, such that said element may be withdrawn from the proximal end of said device by pulling on said connecting link.

13. A method according to claim 12, wherein said connecting link is any one of an electric cable, a cord, and a fluid conveying tube.

14. A method according to claim 12, wherein said element is adapted for multiple use, and said device is adapted for a single-use.

15. A device according to claim 10, wherein said element comprises at least one of a camera head, a steering mechanism, an electronic, magnetic or ultrasound probe or sensor, and a spectral analyzer.

* * * * *